US012699095B2

(12) United States Patent　　　　(10) Patent No.:　US 12,699,095 B2
Bruey et al.　　　　　　　　　　　　　(45) Date of Patent:　　　Aug. 4, 2026

(54) CANCER DIAGNOSIS USING KI-67

(71) Applicant: Quest Diagnostics Investments LLC, Secaucus, NJ (US)

(72) Inventors: Jean Marie Bruey, Encinitas, CA (US); Maher Albitar, Coto De Caza, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 937 days.

(21) Appl. No.: 16/736,325

(22) Filed: Jan. 7, 2020

(65) Prior Publication Data

US 2020/0209242 A1　　Jul. 2, 2020

Related U.S. Application Data

(63) Continuation of application No. 12/610,201, filed on Oct. 30, 2009, now abandoned.

(60) Provisional application No. 61/110,942, filed on Nov. 3, 2008.

(51) Int. Cl.
　　*G01N 33/575*　　　(2026.01)
　　*G01N 33/57505*　　(2026.01)

(52) U.S. Cl.
　　CPC ..... *G01N 33/575* (2026.01); *G01N 33/57505* (2026.01); *G01N 2800/52* (2013.01); *G01N 2800/56* (2013.01)

(58) Field of Classification Search
　　CPC .......... G01N 33/574; G01N 33/57426; G01N 2800/52; G01N 2800/56
　　See application file for complete search history.

(56) References Cited

U.S. PATENT DOCUMENTS

| | | | | |
|---|---|---|---|---|
| 5,558,834 | A | * 9/1996 | Chu ..................... | G01N 33/525 436/66 |
| 5,866,007 | A | * 2/1999 | Whitson ............. | B01L 3/50853 210/488 |
| 2006/0063190 | A1 | 3/2006 | Fischer et al. | |
| 2008/0026394 | A1 | 1/2008 | Labgold et al. | |
| 2008/0058316 | A1 | 3/2008 | Eberhart et al. | |
| 2008/0076134 | A1 | 3/2008 | Muraca | |
| 2009/0253583 | A1 | 10/2009 | Yoganathan | |

OTHER PUBLICATIONS

Bruey et al., (Clin. Cancer Research 14 (19_Supplement): B36, Sep. 22-25, 2008).*
City of Hope Publication, 5 pages, 2023.*
He et al. Ki-67 is a valuable prognostic predictor of lymphoma but its utility varies in lymphoma subtypes: evidence from a systematic meta-analysis. BMC Cancer 14, 153 (published Mar. 5, 2014).*
Neglia et al. (N. Engl. J. Med. 325: 1330-1336, published Nov. 7, 1991).*

Bruey et al., "Circulating Ki-67 protein in plasma as a biomarker and prognostic indicator of acute lymphoblastic leukemia," Leukemia Research 34:173-176 (2010).
Bruey et al., "Clinical Significance of Circulating Ki-67 Protein and Caspase-3 Activity Levels in Chronic Myeloid Leukemia," Blood (ASH Annual Meeting Abstracts) 2009 114: Abstract 4249 (Nov. 2009).
Bruey et al., "Clinical Significance of Circulating Ki-67 Protein and Caspase-3 Activity Levels in Patients with Acute Myeloid Leukemia," Blood (ASH Annual Meeting Abstracts) 2009 114: Abstract 3104 (Nov. 2009).
Bruey et al., "Measuring plasma circulating Ki-67 protein as a biomarker and demonstration of its potential in predicting outcome in Acute Lymphoblastic Leukemia," Blood (ASH Annual Meeting Abstracts) 2009 114: Abstract (Nov. 2009).
Bruey et al., "Plasma Circulating Ki-67 Index as a Biomarker and Prognostic Indicator in Patients with Chronic Lymphocytic Leukemia," Blood (ASH Annual Meeting Abstracts) 2009 114: Abstract 1261 (Nov. 2009).
Bruey et al., Measuring plasma circulating Ki-67 protein as a biomarker and demonstration of its potential in predicting outcome in Acute Lymphoblastic Leukemia, Hematology, Quest Diagnostics Nicols Institute, San Juan Capistrano, CA and Leukemia Departments, M.D. Anderson Cancer Center, University of Texas, Houston, TX and Cancer Therapy and Research Center and University of Texas Health Science Center, San Antonio, Texas, 2010.
Chilosi et al., CD 138/syndecan-1: a useful immunohistochemical marker of normal and neoplastic plasma cells on routine trephine bone marrow biopsies, Mod Pathol. 12 (12):1101-6 (1999).
Diamandis, "Cancer biomarkers: Can we turn recent failures into success?", JNCI, 2010, 102:1462-1467.
Diop et al., Expression of proliferation marker Ki 67 in chronic lymphocytic leukemia, Dakar Med. 50(2):65-8 (2005). Abstract only.
Drach et al., Simultaneous flow cytometric analysis of surface markers and nuclear Ki-67 antigen in leukemia and lymphoma, Cytometry (10(6):743-9 (1989).
Ellegaard et al., Scand. J. Haematol., 1980, 25:275-285.
Fusco et al., Prognostic significance of the ki-67 labeling index in growth hormone-secreting pituitary adenomas, J Clin Endocrinol Metab. 93(7):2746-50 (2008).
Gala et al., High expression of bcl-2 is the rule in acute lymphoblastic leukemia, except in Burkitt subtype at presentation, and is not correlated with the prognosis, Ann Hematol. 69(1):17-24 (1994).
Gerdes et al., Cell Cycle Analysis Of A Cell Proliferation-Associated Human Nuclear Antigen Defined By The Monoclonal Antibody Ki-671, The Journal of Immunology, 133(4):1710-1715, (1984).
Giles et al., A prognostic model for survival in chronic lymphocytic leukaemia based on p53 expression, Br. J. Haemotal., 121:578-585, (2003).
Girino et al., Monoclonal antibody Ki-67 as a marker of proliferative activity in monoclonal gammopathies, Acta Haematol., 85(1)26-30, (1991).

(Continued)

*Primary Examiner* — Alana Harris Dent
(74) *Attorney, Agent, or Firm* — DUANE MORRIS LLP

(57) ABSTRACT

The present invention provides methods and compositions for detection, diagnosis, prognosis, monitoring treatment and monitoring progression of cancer by detecting the level of Ki-67 protein in an individual.

13 Claims, 13 Drawing Sheets

Specification includes a Sequence Listing.

(56)          References Cited

OTHER PUBLICATIONS

Greil et al., Expression of the c-myc proto-oncogene in multiple myeloma and chronic lymphocytic leukemia: an in situ analysis, Blood 78(1):180-91 (1991).

Hazenberg et al., T-cell division in human immunodeficiency virus (HIV)-1 infection is mainly due to immune activation: a longitudinal analysis in patients before and during highly active antiretroviral therapy (HAART), 2000, Blood, 95:249-255.

Heyden et al., Cytoplasmatic observation of the Ki-67 protein and immuno fluorescent staining of its transport to the nucleus. Eur. J. Cell Biol., Supplement 42, vol. 69, p. 32 (1996). Abstract only.

International Search Report for PCT Patent Application No. PCT/US2009/062877, International filing date: Oct. 30, 2009.

Jaroslav et al., Expression of cyclins D1, D2 and D3 and Ki-67 in human leukemia, Leukemia & Lymphoma 46(11):1605-1612, (2005).

Kanavaros et al., Expression of p53, p21/waf1, bcl-2, bax, Rb and Ki67 proteins in Hodgkin's lymphomas, Histol Histopathol. 15(2):445-53 (2000).

Landberg et al., Flow cytometric multiparameter analysis of proliferating cell nuclear antigen/cyclin and Ki-67 antigen: a new view of the cell cycle, Exp. Cell Res. 187(1):111-8 (1990).

Larsson et al., Expression of the c-myc protein is down-regulated at the terminal stages during in vitro differentiation of B-type chronic lymphocytic leukemia cells, Blood 77(5): 1025-32 (1991).

Lokhorst et al., Determination of the growth fraction in monoclonal gammopathy with the monoclonal antibody Ki-67, Br. J. Haematology, 69(4):477-481, (1988).

Markovic et al., Expression of VEGF and microvessel density in patients with multiple myeloma: clinical and prognostic significance, Med Oncol. [Epub ahead of print] May 1, 2008.

Miguel-Garcia et al., Circulating Ki67 positive lymphocytes in multiple myeloma and benign monoclonal gammopathy. J. Clin. Path., 48:835-839 (1995).

Nakao et al., Genetic and clinical studies of serum $\beta_2$-microglobulin levels in haematological malignancies, Clini. Exp. Immunol. 45:134-141 (1981).

Oh et al., Expression of functional markers in acute lymphoblastic leukemia, Leuk Res. 27:903-908 (2003).

Pellegrini et al., Assessment of cell proliferation in normal and pathological bone marrow biopsies: a study using double sequential immunophenotyping on paraffin sections, Histopathology 27(5):397-405 (1995).

Rykova et al., Breast cancer diagnostic based on extracellular DNA and RNA circulating in blood, Biomed Khim, 54(1):94-103 (2008)—English abstract only.

Satoh et al., "Increased levels of KL-6 and subsequent mortality in patients with interstitial lung disease," Journal of Internal Medicine, 2006, 260:429-434.

Schluter et al., The cell proliferation-associated antigen of antibody Ki-67: a very large, ubiquitous nuclear protein with numerous repeated elements, representing a new kind of cell cycle-maintaining proteins, J. Cell. Biol., 123(3):513-522 (1993).

Schwarzenbach et al., A critical evaluation of loss of heterozygosity detected in tumor tissues, blood serum and bone marrow from patients with breast cancer, Breast Cancer Research, 9(5):R66 (2007). (8 pgs.).

Starborg et al., The murine Ki-67 cell proliferation antigen accumulates in the nucleolar and heterochromatic regions of interphase cells and at the periphery of the mitotic chromosomes in a process essential for cell cycle progression, J. Cell Sci., 109:143-153, (1996).

Van Dierendonck et al., Cell-cycle-related staining patterns of anti-proliferating cell nuclear antigen monoclonal antibodies. Comparison with BrdUrd labeling and ki-67 staining, Am J Pathol. 138(5):1165-72 (1991).

Vrzogic et al., Effect of napthalan on epidermal proliferation activity and CD3, CD4, and CD8 lymphocyte count. Acta Dermatovenerol Croat., 11(2):65-9 (2003).

White et al., Assessment of proliferative activity in leukaemic bone marrow using the monoclonal antibody Ki-67, J. Clin. Pathol 47(3): 209-213, (1994).

Xu et al., Expression of Ki-67 and Bcl-2 in Adults and Children with Acute Lymphoblastic Leukemia and Its Clinical Significance, J Exp Hematol. 14(5):887-890, (2006).—(Article in Chinese with English abstract).

Yamanaka et al., The prognostic value of Ki-67 antigen in non-Hodgkin lymphoma of Waldeyer ring and the nasal cavity. Cancer, 70(9):2342-9 (1992).

Jaffe, Elaine et al. "Classification of lymphoid neoplasms: the microscope as a tool for disease discovery." Blood 112 (12):4384-4399 (2008), 16 pages.

Alizadeh, Ash et al. "Distinct types of diffuse large B-cell lymphoma identified by gene expression profiling." Nature 403: 503-511 (2000), 9 pages.

Hecht, Jonathan and Aster, Jon. "Molecular Biology of Burkitt's Lymphoma." Journal of Clinical Oncology 18(21):3707-3721 (2000), 15 pages.

Brunning, Richard. "Classification of Acute Leukemias" Seminars in Diagnostic Pathology. 20(3): 142-153 (2003), 12 pages.

Pui, Ching-Hon and Evans, William. "Treatment of Acute Lymphoblastic Leukemia" New England Journal of Medicine. 354(2):166-178 (2006), 13 pages.

Canellos, George. "Lymphoma: Present and Future Challenges." Seminars in Hematology. 41(suppl 7): 26-31 (2004), 6 pages.

* cited by examiner

Ki-67 in acute lymphoblastic leukemia patients

FIG. 2: **Homo sapiens Ki-67 amino acid sequence;
GenBank Accession No. NM_002417**

```
MWPTRRLVTIKRSGVDGPHFPLSLSTCLFGRGIECDIRIQLPVV
SKQHCKIEIHEQEAILHNFSSTNPTQVNGSVIDEPVRLKHGDVITIIDRSFRYENESL
QNGRKSTEFPRKIREQEPARRVSRSSFSSDPDEKAQDSKAYSKITEGKVSGNPQVHIK
NVKEDSTADDSKDSVAQGTTNVHSSEHAGRNGRNAADPISGDFKEISSVKLVSRYGEL
KSVPTTQCLDNSKKNESPFWKLYESVKKELDVKSQKENVLQYCRKSGLQTDYATEKES
ADGLQGETQLLVSRKSRPKSGGSGHAVAEPASPEQELDQNKGKGRDVESVQTPSKAVG
ASFPLYEPAKMKTPVQYSQQQNSPQKHKNKDLYTTGRRESVNLGKSEGFKAGDKTLTP
RKLSTRNRTPAKVEDAADSATKPENLSSKTRGSIPTDVEVLPTETEIHNEPFLTLWLT
QVERKIQKDSLSKPEKLGTTAGQMCSGLPGLSSVDINNFGDSINESEGIPLKRRRVSF
GGHLRPELFDENLPPNTPLKRGEAPTKRKSLVMHTPPVLKKIIKEQPQPSGKQESGSE
IHVEVKAQSLVISPPAPSPRKTPVASDQRRRSCKTAPASSSKSQTEVPKRGGRKSGNL
PSKRVSISRSQHDILQMICSKRRSGASEANLIVAKSWADVVKLGAKQTQTKVIKHGPQ
RSMNKRQRRPATPKKPVGEVHSQFSTGHANSPCTIIIGKAHTEKVHVPARPYRVLNNF
ISNQKMDFKEDLSGIAEMFKTPVKEQPQLTSTCHIAISNSENLLGKQFQGTDSGEEPL
LPTSESFGGNVFFSAQNAAKQPSDKCSASPPLRRQCIRENGNVAKTPRNTYKMTSLET
KTSDTETEPSKTVSTANRSGRSTEFRNIQKLPVESKSEETNTEIVECILKRGQKATLL
QQRREGEMKEIERPFETYKENIELKENDEKMKAMKRSRTWGQKCAPMSDLTDLKSLPD
TELMKDTARGQNLLQTQDHAKAPKSEKGKITKMPCQSLQPEPINTPTHTKQQLKASLG
KVGVKEELLAVGKFTRTSGETTHTHREPAGDGKSIRTFKESPKQILDPAARVTGMKKW
PRTPKEEAQSLEDLAGFKELFQTPGPSEESMTDEKTTKIACKSPPPESVDTPTSTKQW
PKRSLRKADVEEEFLALRKLTPSAGKAMLTPKPAGGDEKDIKAFMGTPVQKLDLAGTL
PGSKRQLQTPKEKAQALEDLAGFKELFQTPGHTEELVAAGKTTKIPCDSPQSDPVDTP
TSTKQRPKRSIRKADVEGELLACRNLMPSAGKAMHTPKPSVGEEKDIIIFVGTPVQKL
DLTENLTGSKRRPQTPKEEAQALEDLTGFKELFQTPGHTEEAVAAGKTTKMPCESSPP
ESADTPTSTRRQPKTPLEKRDVQKELSALKKLTQTSGETTHTDKVPGGEDKSINAFRE
TAKQKLDPAASVTGSKRHPKTKEKAQPLEDLAGLKELFQTPVCTDKPTTHEKTTKIAC
RSQPDPVDTPTSSKPQSKRSLRKVDVEEEFFALRKRTPSAGKAMHTPKPAVSGEKNIY
AFMGTPVQKLDLTENLTGSKRRLQTPKEKAQALEDLAGFKELFQTRGHTEESMTNDKT
AKVACKSSQPDPDKNPASSKRRLKTSLGKVGVKEELLAVGKLTQTSGETTHTHTEPTG
DGKSMKAFMESPKQILDSAASLTGSKRQLRTPKGKSEVPEDLAGFIELFQTPSHTKES
MTNEKTTKVSYRASQPDLVDTPTSSKPQPKRSLRKADTEEEFLAFRKQTPSAGKAMHT
PKPAVGEEKDINTFLGTPVQKLDQPGNLPGSNRRLQTRKEKAQALEELTGFRELFQTP
CTDNPTTDEKTTKKILCKSPQSDPADTPTNTKQRPKRSLKKADVEEEFLAFRKLTPSA
GKAMHTPKAAVGEEKDINTFVGTPVEKLDLLGNLPGSKRRPQTPKEKAKALEDLAGFK
ELFQTPGHTEESMTDDKITEVSCKSPQPDPVKTPTSSKQRLKISLGKVGVKEEVLPVG
KLTQTSGKTTQTHRETAGDGKSIKAFKESAKQMLDPANYGTGMERWPRTPKEEAQSLE
DLAGFKELFQTPDHTEESTTDDKTTKIACKSPPPESMDTPTSTRRRPKTPLGKRDIVE
ELSALKQLTQTTHTDKVPGDEDKGINVFRETAKQKLDPAASVTGSKRQPRTPKGKAQP
LEDLAGLKELFQTPICTDKPTTHEKTTKIACRSPQPDPVGTPTIFKPQSKRSLRKADV
EEESLALRKRTPSVGKAMDTPKPAGGDEKDMKAFMGTPVQKLDLPGNLPGSKRWPQTP
KEKAQALEDLAGFKELFQTPGTDKPTTDEKTTKIACKSPQPDPVDTPASTKQRPKRNL
RKADVEEEFLALRKRTPSAGKAMDTPKPAVSDEKNINTFVETPVQKLDLLGNLPGSKR
QPQTPKEKAEALEDLVGFKELFQTPGHTEESMTDDKITEVSCKSPQPESFKTSRSSKQ
RLKIPLVKVDMKEEPLAVSKLTRTSGETTQTHTEPTGDSKSIKAFKESPKQILDPAAS
VTGSRRQLRTRKEKARALEDLVDFKELFSAPGHTEESMTIDKNTKIPCKSPPPELTDT
ATSTKRCPKTRPRKEVKEELSAVERLTQTSGQSTHTHKEPASGDEGIKVLKQRAKKKP
NPVEEEPSRRRPRAPKEKAQPLEDLAGFTELSETSGHTQESLTAGKATKIPCESPPLE
VVDTTASTKRHLRTRVQKVQVKEEPSAVKFTQTSGETTDADKEPAGEDKGIKALKESA
KQTPAPAASVTGSRRRPRAPRESAQAIEDLAGFKDPAAGHTEESMTDDKTTKIPCKSS
PELEDTATSSKRRPRTRAQKVEVKEELLAVGKLTQTSGETTHTDKEPVGEGKGTKAFK
QPAKRKLDAEDVIGSRRQPRAPKEKAQPLEDLASFQELSQTPGHTEELANGAADSFTS
APKQTPDSGKPLKISRRVLRAPKVEPVGDVVSTRDPVKSQSKSNTSLPPLPFKRGGGK
DGSVTGTKRLRCMPAPEEIVEELPASKKQRVAPRARGKSSEPVVIMKRSLRTSAKRIE
PAEELNSNDMKTNKEEHKLQDSVPENKGISLRSRRQNKTEAEQQITEVFVLAERIEIN
RNEKKPMKTSPEMDIQNPDDGARKPIPRDKVTENKRCLRSARQNESSQPKVAEESGGQ
KSAKVLMQNQKGKGEAGNSDSMCLRSRKTKSQPAASTLESKSVQRVTRSVKRCAENPK
KAEDNVCVKKIRTRSHRDSEDI
```

RLU

CANCER DIAGNOSIS USING KI-67

CROSS-REFERENCE TO RELATED APPLICATIONS

This application is a Continuation of U.S. application Ser. No. 12/610,201, filed Oct. 30, 2009, which claims the benefit of U.S. Provisional Applications 61/110,942, filed Nov. 3, 2008 which is hereby incorporated by reference in its entirety.

The instant application contains a Sequence Listing which has been submitted in ASCII format via EFS-WEB and is hereby incorporated by reference in its entirety. Said ASCII copy, created on Dec. 30, 2019, is named sequence.txt and is 28,996 bytes.

FIELD OF THE INVENTION

Provided are methods and compositions related to the field of disease detection and, more specifically, for determining a diagnosis and/or prognosis of patients having hyperproliferative disorders.

BACKGROUND OF THE INVENTION

The following description is provided to assist the reader in understanding the invention and is not admitted to describe or constitute prior art to the invention.

Human Ki-67 protein is expressed in nuclei of proliferating cells in all active phases of the cell cycle, i.e. in G1, S, G2 and mitosis, but not in quiescent G0 cells (Gerdes et al., J. Immunol. 133:1710-1715 (1984)). The cDNA of human Ki-67 and of the murine equivalent are known and show no significant homologies to other proteins (Schluter et al., J. Cell Biol. 123:513-522 (1993); Starborg et al., J. Cell Sci. 109:143-153 (1996)). Human Ki-67 protein has several nuclear localization signals and can physiologically be detected in the cell nucleus, except during mitosis (Heyden et al., Eur. J. Cell Biol. 42: 33 (1996)).

Acute lymphoblastic leukemia (ALL) is a form of leukemia (cancer of white blood cells) in which immature white blood cells rapidly multiply and crowd out normal cells in bone marrow. These immature cells do not develop into lymphocytes, which the body uses to fight infection. The immature white blood cells can spread throughout the body and adversely affect other organs. There are about 4,000 new cases of ALL in the United States each year. The earlier acute lymphoblastic leukemia is detected, the more effective the treatment.

White, et al., detects Ki-67 protein in bone marrow cells (J. Clin. Pathol 47(3): 209-13 (1994)). Jaroslav, et al., detect Ki-67 protein in chronic myelogenous leukemia (CML), ALL, acute myeloid leukemia (AML) and chronic lymphocytic leukemia (CLL) cells (Leuk Lymphoma 46(11): 1605-1612 (2005)). Xu, et al., detect Ki-67 protein by immunohistochemical staining in cells of children and adults with ALL (Zhonggou Shi Yan Xue Ye Xue Za Zhi 14(6): 887-890 (2006)). Rykova, E., et al., describes the detection of Ki-67 RNA in plasma and cell bound fraction of patients with breast cancer (Ann. NY Acad. Sci. 1075: 328-333 (2006)). U.S. Patent Application No. 2008/0026394 describes electrochemical detection of cancer markers.

SUMMARY OF THE INVENTION

The present invention provides methods and compositions for detection, diagnosis, prognosis, monitoring treatment and monitoring progression of cancer (e.g., a leukemia or lymphoma) in an individual by assessing Ki-67 protein in an acellular body fluid sample. As described herein, plasma Ki-67 reflects the entire body and not just the site of biopsy so provides information on tumor load, and/or provide more reproducible results.

In one aspect, the invention provides a method for diagnosing an individual as having leukemia or lymphoma by determining the level of Ki-67 protein in an acellular body fluid sample (e.g., serum or plasma) from the individual; comparing the measured level of Ki-67 protein from the individual to a pre-determined cutoff value, and identifying the individual as having leukemia or lymphoma when the Ki-67 protein level of the individual is higher than the cutoff value. Suitable cutoff levels may be determined based on the particular acellular body fluid sample assessed and the particular analytical technique used. Generally, suitable cutoff levels for diagnosis when using plasma are about 900-1500 U Ki-67/ml (e.g., about 1000, 1100, 1200, 1300, or 1400 U/ml). Optionally, the level of β2-microglobulin is also measured, wherein an elevated level compared to disease-free individuals is further diagnostic of leukemia or lymphoma.

The invention also provides a method for diagnosing an individual as having leukemia or lymphoma by measuring the level of Ki-67 protein in an acellular body fluid sample from the individual; calculating a Ki-67 index by normalizing the measured amount of Ki-67 protein to be expressed on a per cell (i.e., per lymphocyte) basis; comparing the Ki-67 index to a pre-determined cutoff value, and identifying the individual as having leukemia when the Ki-67 protein index is higher than said cutoff value. Suitable cutoff values are about 1.5-2.25 U/1000 lymphocytes (e.g., about 1.75, 1.88, 1.95, 2.0, 2.1, 2.2 U/1000 lymphocytes). In this embodiment, the Ki-67 index is calculated by dividing the concentration of Ki-67 (i.e., U/μl) by the concentration of lymphocytes in the same volume. The index may be expressed, for example, as units of Ki-67 per 1000 lymphocytes.

The invention also provides a method for determining the prognosis of an individual with leukemia by measuring the level of Ki-67 protein in an acellular body fluid sample from the individual; calculating a Ki-67 index (e.g., by normalizing the measured amount of Ki-67 protein to the concentration of lymphocytes); comparing the Ki-67 index to a pre-determined cutoff value, and identifying the individual as having a poor prognosis when the Ki-67 protein index is higher than said cutoff value. The prognosis for the individual may be expressed as survival time, complete remission, or remission duration. The blood parameter used to normal the amount of Ki-67 may be the number of total lymphocytes or the number of lymphocytes per unit volume of the blood sample. Suitable cutoff values are about 1.5-2.25 U/1000 lymphocytes/μl (e.g., about 1.75, 1.88, 1.95, 2.0, 2.1, 2.2 U/1000 lymphocytes).

The invention also provides a method for modifying the dosage of chemotherapy administered to an individual diagnosed as having leukemia or lymphoma by determining a Ki-67 protein level index in a first acellular body fluid sample from the individual; determining the Ki-67 protein index in a second acellular body fluid sample from the individual, wherein said second sample is obtained at a later time than said first sample, wherein chemotherapy is administered between obtaining the first and second sample; and modifying said dosage of chemotherapy based on the difference in the Ki-67 protein index in the second sample relative to the first sample, wherein the dosage of chemotherapy in increased when the Ki-67 protein index is higher in the second sample compared to the first sample or reducing or maintaining the dosage of chemotherapy when the Ki-67 protein index is lower in the second sample compared to the first sample. The Ki-67 protein index may be the concentration of Ki-67 protein in the acellular body fluid, or it may be the concentration of Ki-67 protein in the acellular body fluid normalized to the concentration of lymphocytes per unit volume of the acellular body fluid. In one embodiment, the individual is diagnosed as having CML in the chronic phase. In other embodiments, the chemotherapy is Chlorambucil, Cytoxan, or Fludarabine.

In any of the inventive methods, the leukemia or lymphoma may be non-Hodgkin's lymphoma (NHL), acute lymphoblastic leukemia (ALL), Burkitt's lymphoma, acute myeloid leukemia (AML), acute undifferentiated leukemia (AUL), chronic lymphocytic leukemia (CLL), or chronic myeloid leukemia (CML).

One of skill in the art would readily recognize that the measurement of Ki-67 protein can be accomplished using various types of assays well-known in the art. In preferred embodiments, Ki-67 protein is detected using a specific binding agent, preferably an antibody. In another embodiment, the assay is an immunoassay such as an enzyme-linked immunosorbent assay (ELISA) or sandwich-type ELISA. In another embodiment, the assay can be flow cytometry. In the later case, a sandwich-type assay involving capture of an antibody-antigen complex on a bead or microparticle and binding of a labeled second antibody can provide useful assay materials to be evaluated by flow cytometry. In other embodiments, Ki-67 protein is detected by immunoprecipitation which separates proteins from other molecules in the sample. In other embodiments, the measurement of Ki-67 protein is accomplished by immunoblot. In yet other embodiments, the measurement of Ki-67 protein is accomplished by electrochemiluminescence such as by the Meso Scale Discovery (MSD) system. In other embodiments, the Ki-67 protein is detected using protein microarray platform. In one embodiment, the Ki-67 protein is captured directly on microarray solid surface. In another embodiment, the Ki-67 protein is captured is captured indirectly on the microarray solid surface such as through antibody.

"Ki-67 protein" is a marker associated with cancer, as recognized by specific sets of antibodies, which may be used to identify the cell type, stage of differentiation and activity state of a cell. Ki-67 protein and antibodies for detecting Ki-67 protein are described in for example, White, D. M., et al. 47 J. Clin. Pathol. 209-213 (1994); Schwarzenbach, H., et al., 9(5) Breast Cancer Research R66 (2007); Lokhorst, H. M., et al., 69(4) Br. J. Haematology 477-481 (1988); Girino M., et al., 85(1) Acta Haematology 26-30 (1991); and Genbank Accession No. NM_002417. In certain embodiments, Ki-67 protein is present in the liquid phase of a bodily fluid and which remain in the liquid phase after cells have been removed from the bodily fluid (i.e. an acellular body fluid). Ki-67 protein includes fragments of the native cell Ki-67 protein and/or Ki-67 may be physically associated with other biomolecules in the body fluid.

The term "level" as used herein refers to an amount or a concentration of Ki-67 protein. Typically, the level of Ki-67 protein will be expressed as a concentration, or an absolute amount of Ki-67 protein per volume or weight. The term "elevated levels" refers to levels of Ki-67 protein that are above the range of the reference value. In some embodiments, patients with "high" or "elevated" Ki-67 protein levels have activity levels that are higher than the median activity in a population of patients with that disease. In certain embodiments, "high" or "elevated" Ki-67 protein levels for a patient with a particular disease refers to levels that are above the median values for patients with that disorder and are in the upper 40% of patients with the disorder, or to levels that are in the upper 20% of patients with the disorder, or to levels that are in the upper 10% of patients with the disorder, or to levels that are in the upper 5% of patients with the disorder.

The term "determining the level of Ki-67" as used herein refers to measuring or otherwise assessing the amount of the Ki-67 protein in an acellular body fluid obtained from an individual. The assessment of Ki-67 protein level may be relative (e.g., expressed as greater or less than a reference standard or amount, or merely as the presence or absence of a detectable amount) or absolute (e.g., expressed as a concentration). Optionally, when used for detection, prognosis or monitoring cancer, the level of Ki-67 protein in a sample from an individual is compared to the Ki-67 protein level determined in a corresponding sample from person(s) without cancer, known to suffer from, or known to be at risk of a cancer. When determining an individual's prognosis, the level of Ki-67 protein in a sample from an individual diagnosed with cancer is compared to the Ki-67 level determined in a corresponding sample from individuals diagnosed with the same cancer for which the outcome of the cancer is known. In certain embodiments, a threshold (cut-off) level of Ki-67 protein may be established for a given diagnosis or prognosis, and the level of Ki-67 protein in an individual's sample can simply be compared to the threshold level.

The term "circulating Ki-67 index" as used herein refers to a value obtained by determining the ratio of the level of Ki-67 value per given number of lymphocytes/unit volume of acellular body fluid. In one embodiment, circulating Ki-67 index is determined by obtaining a ratio of the Ki-67 level per 1000 lymphocytes. The circulating Ki-67 index value may be indicative of prognosis of cancer patients. Exemplary cancers include but not limited to CLL, ALL, AML, CML, AUL.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. There are many ways that prognosis can be expressed. For example prognosis can be expressed in terms of complete remission rates (CR), overall survival (OS) which is the amount of time from entry to death, remission duration, which is the amount of time from remission to relapse or death.

The phrase "determining the prognosis" as used herein refers to the process by which the practitioner can predict the course or outcome of a condition in an individual. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

In one embodiment, prognosis of CLL patients can be expressed based on the Rai staging system. According to Rai staging system, status of CLL patients can be divided into 5 stages 0-IV. Stage 0 indicates there are too many lymphocytes in the blood, but there are usually no other symptoms of leukemia. Lymph nodes and the spleen and liver are not swollen, and the number of red blood cells and platelets is normal. Stage I indicates there are too many lymphocytes in the blood and lymph nodes are swollen (lymphadenopathy). The spleen and liver are not swollen and the number of red blood cells and platelets is normal. Stage II indicates there are too many lymphocytes in the blood, lymph nodes are swollen, and either the liver is swollen (hepatomegaly) or the spleen is swollen (splenomegaly). Stage III indicates there are too many lymphocytes in the blood and too few red blood cells (anemia). Lymph nodes and the liver or spleen may be swollen. Stage IV indicates there are too many lymphocytes in the blood and too few platelets (thrombocytopenia). The lymph nodes, liver, or spleen may be swollen, and there may be too few red blood cells (anemia).

The phrase "specific binding agent" as used herein refers to any agent, molecule, or compound that specifically binds Ki-67 protein or portion thereof. Examples include, but are not limited to, antibodies or antibody fragments, ligands, or receptors. These binding agents could be naturally occurring or synthetic and include modified or recombinant proteins. In preferred embodiments the specific binding agent is an antibody. See e.g., White, D. M., et al. 47 J. Clin. Pathol. 209-213 (1994); Schwarzenbach, H., et al., 9(5) Breast Cancer Research R66 (2007); Lokhorst, H. M., et al., 69(4) Br. J. Haematology 477-481 (1988); Girino M., et al., 85(1) Acta Haematology 26-30 (1991); and Genbank Accession No. NM_002417.

As used herein, an "acellular body fluid" is a fluid sample, obtained from a subject, which is substantially free of cells and include, for example, amniotic fluid, blood, cerebral spinal fluid, lactal duct fluid, lymph, peritoneal fluid, plasma, pleural fluid, saliva, serum, sputum, tears, and urine. Preferably, an acellular bodily fluid contains less than about 1% (w/w) whole cellular material. Plasma and serum are examples of acellular bodily fluids. A sample may include a specimen of natural or synthetic origin.

As used herein "absolute lymphocyte count" refers to total number of lymphocyte cells per unit volume of blood. In one embodiment the unit volume of blood may be microliter. In another embodiment, the unit volume of blood may be milliliter. In yet another embodiment, the unit volume of blood may be deciliter.

A "reference sample" comprises a sample of bodily fluid with a known Ki-67 level. The reference sample may contain a known absolute amount of Ki-67 such as an external standard used in a detection assay. Alternatively, a reference sample may be from known normal or diseased subjects wherein the Ki-67 level is designated as being "normal" or diseased.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluoresence, or chemiluminescence, electrochemiluminescence or any other appropriate means. Preferred detectable labels include fluorescent dye molecules or fluorophores.

The term "limit of detection (LOD)" as used herein refers to a the point at which a measured value of an analyte in an assay is larger than the uncertainty associated with it. In one embodiment, LOD is defined as 3 standard deviations (SD) from the zero concentration.

The term "about" as used herein in reference to quantitative measurements or values, refers to the indicated value plus or minus 10%.

BRIEF DESCRIPTION OF THE FIGURES

FIG. 2 is the amino acid sequence of Ki-67 protein as provided at Genbank Accession No. NP_002408 (SEQ ID NO: 1).

FIG. 6A shows a Western blot analysis of Ki-67 protein expression levels in cultured cells in presence of serum or in serum starved condition. Beta-actin served as a positive control for the assay. FIG. 6B shows the results of the analysis of cell lysates (in presence of serum versus serum starved) for the detection of Ki-67 protein using MSD® ECL method.

Figure 8:
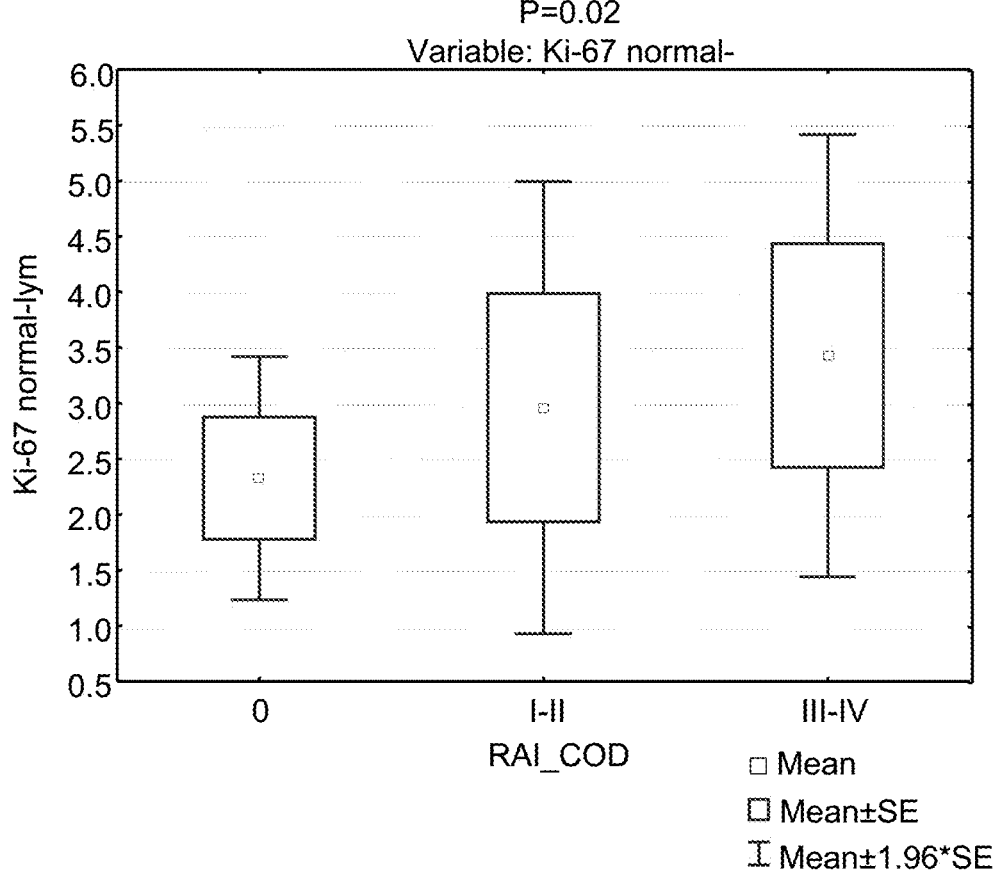

FIG. 8 shows a correlation of the relative Ki-67 level with the prognosis of CLL patients. Prognosis of CLL patients were classified according to Rai classification from 0-IV. Plasma Ki-67 values and absolute lymphocyte count were measured of the CLL patients. A normalized Ki-67 value is obtained by taking the ratio of the Ki-67 level to the absolute lymphocyte count. Normalized Ki-67 values were plotted against the Rai-classified CLL patient groups in box plots. The mean normalized Ki-67 for each group is indicated as a small square within each box. The standard deviation of measurement for each group is indicated.

Figure 9:
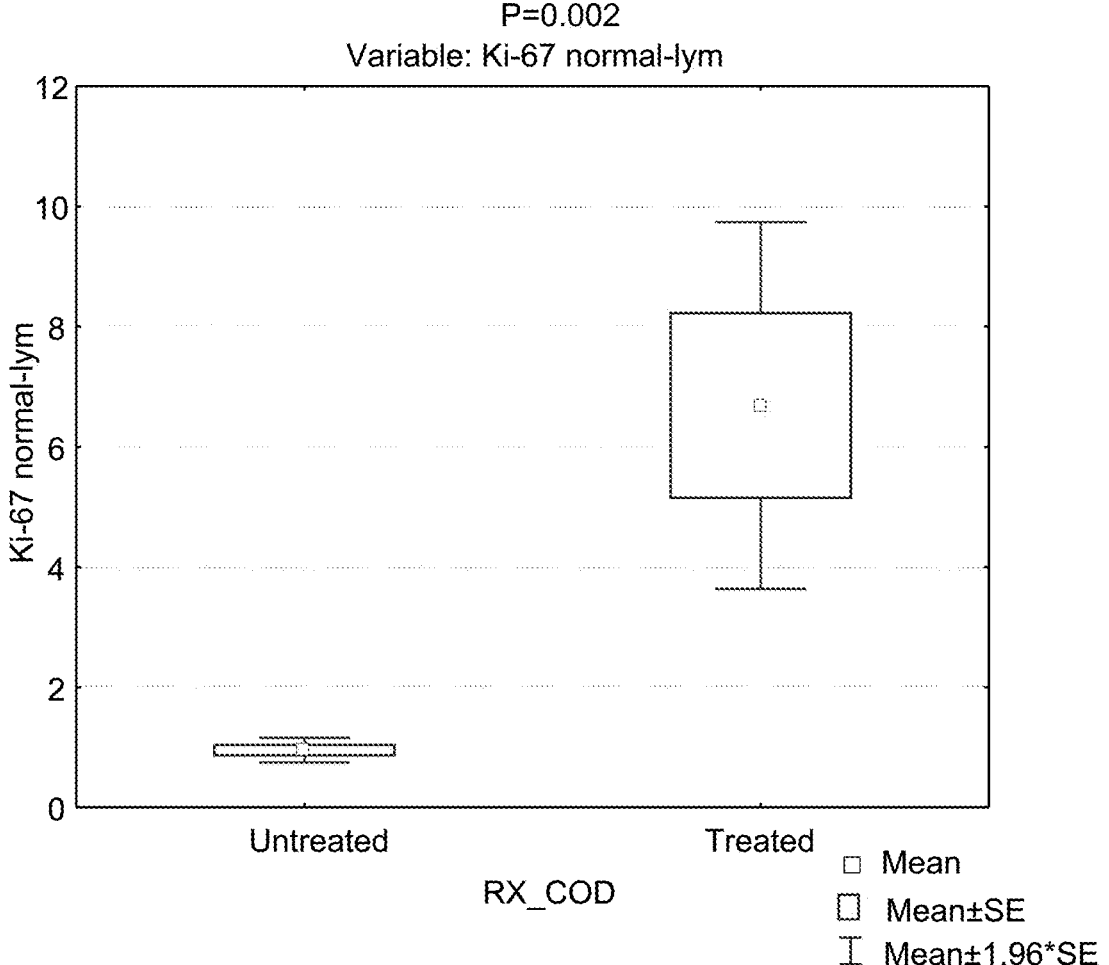

FIG. 9 shows a box plot of the normalized Ki-67 levels in treated and untreated CLL patients. Plasma Ki-67 values and absolute lymphocyte count were measured from CLL patients treated with or without (untreated) Chlorambucil. A normalized Ki-67 value is obtained by taking the ratio of the Ki-67 level to the absolute lymphocyte count. The normalized Ki-67 values were plotted for the treated and untreated groups.

Figure 10:
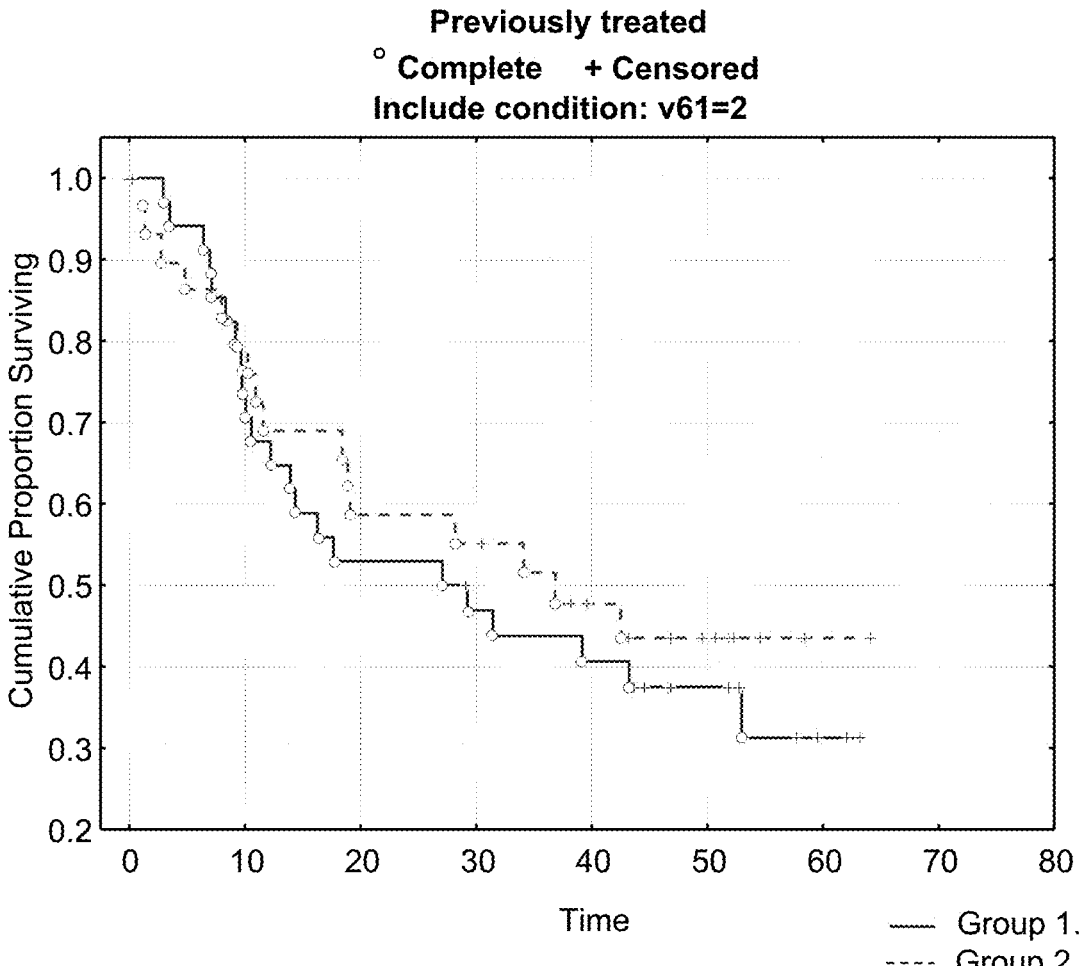

FIG. 10 shows a correlation of survival of CLL patients in months with the normalized level of Ki-67 protein (relative to the number of lymphocytes) in plasma after starting a new therapy. CLL patients were monitored for survival in months from the start of treatment with Cytoxan and Fludarabine. A normalized Ki-67 value is obtained by taking the ratio of the plasma Ki-67 level to the absolute lymphocyte count. The solid line (Group 1) represents the population of individuals with a normalized Ki-67 level of greater than 1.88 U/1000 lymphocytes. The dashed line (Group 2) represents the population of individuals with a normalized Ki-67 value of less than or equal to 1.88 U/1000 lymphocytes. An open circle (o) "complete" indicates dead and a plus (+) "Censored indicates alive.

Figure 11:
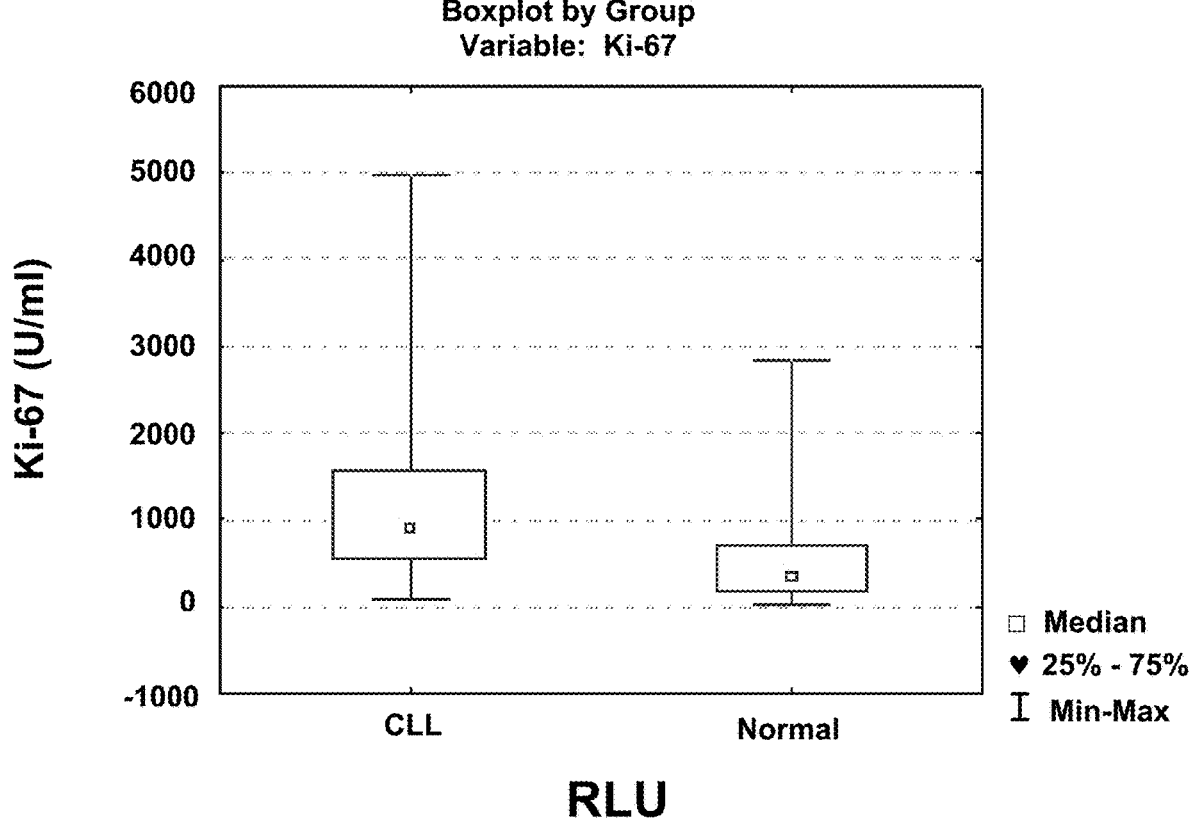

FIG. 11 shows a box plot of the levels of circulating Ki-67 protein in plasma in normal individuals (N) and CLL patients as determined by MSD® Electrochemiluminiscent method. The units of Ki-67 levels are expressed as U/ml. Median values of the levels of Ki-67 protein is represented as a horizontal line within the box in each case.

Figure 12:
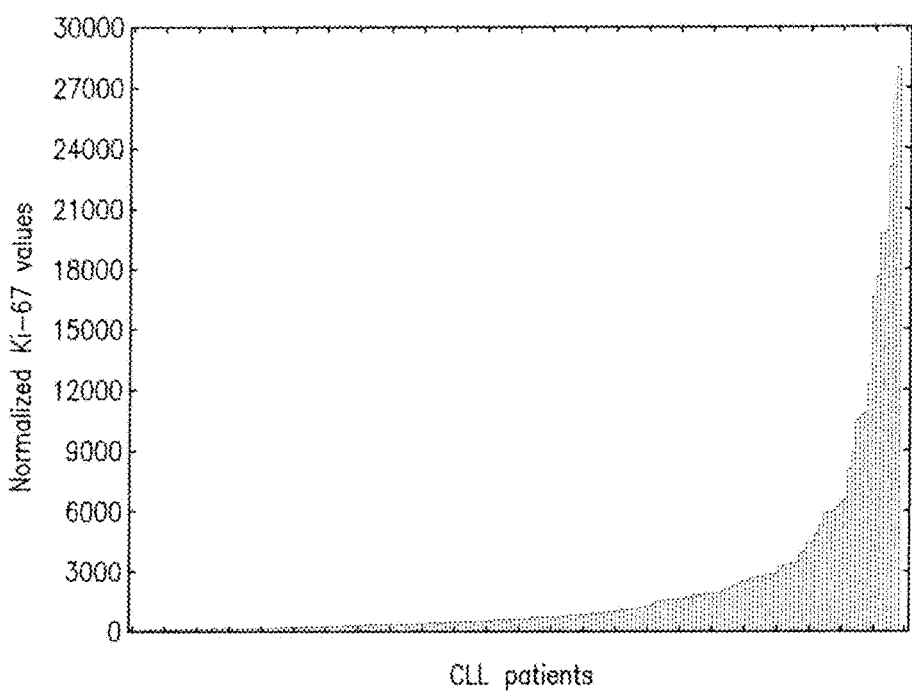

FIG. 12 shows the distribution of normalized Ki-67 values in the plasma of 194 CLL patients. A normalized Ki-67 value is obtained by taking the ratio of the plasma Ki-67 level to the absolute lymphocyte count.

Figure 13:
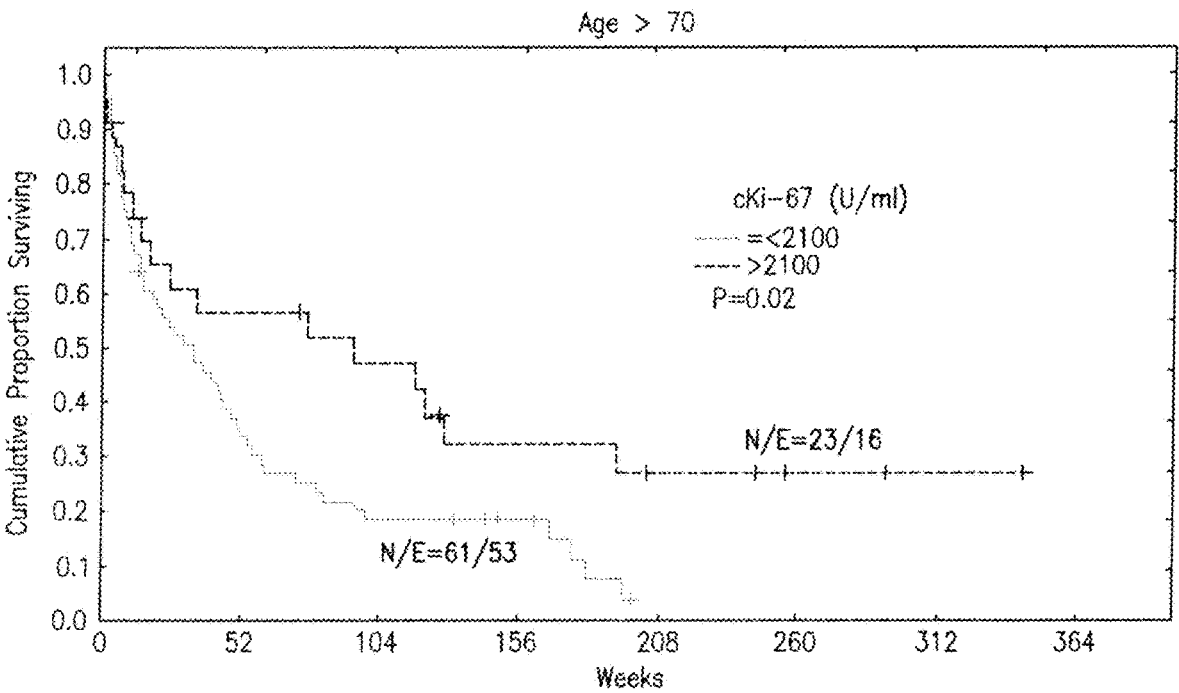

FIG. 13 shows the cumulative proportion of AML patients surviving in two populations of patients: 1) patients having plasma concentration of Ki-67 protein of less than 2100 U/ml (solid line), and 2) patients having plasma concentration of Ki-67 protein of greater than 2100 U/ml (dashed line).

Figure 14:
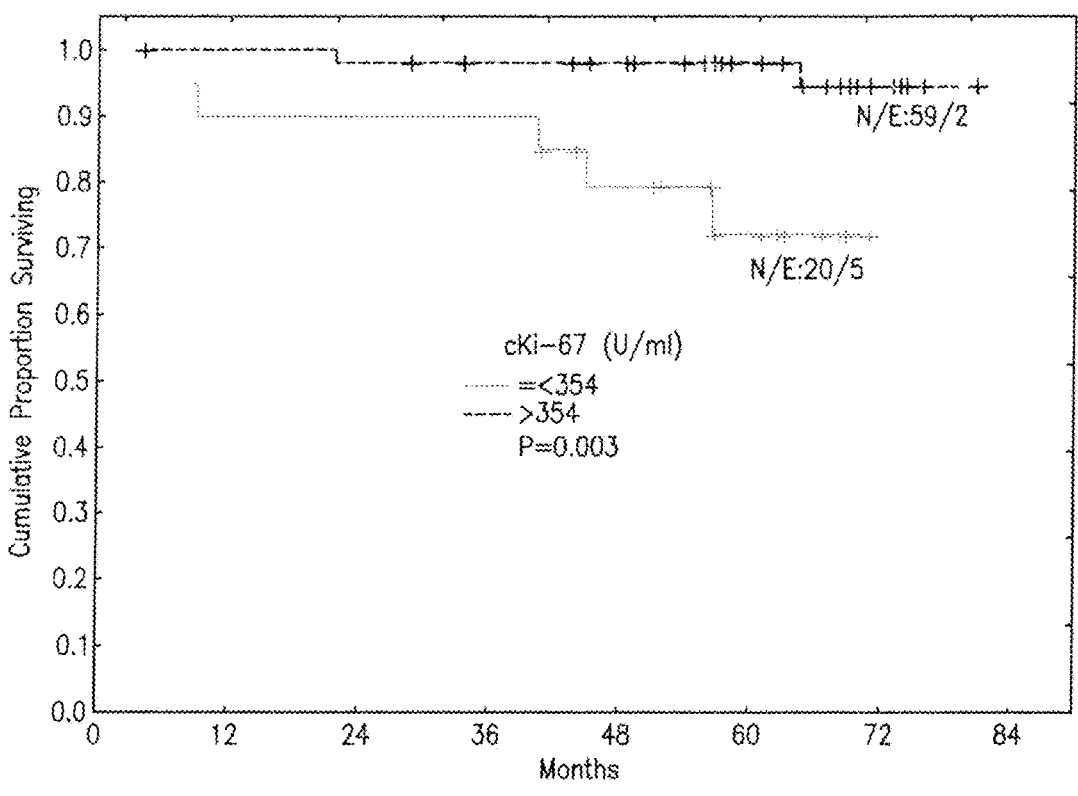

FIG. 14 shows the cumulative proportion of CML patients surviving in two populations of patients: 1) patients having plasma concentration of Ki-67 protein of less than 354 U/ml (solid line), and 2) patients having plasma concentration of Ki-67 protein of greater than 354 U/ml (dashed line).

Figure 15:
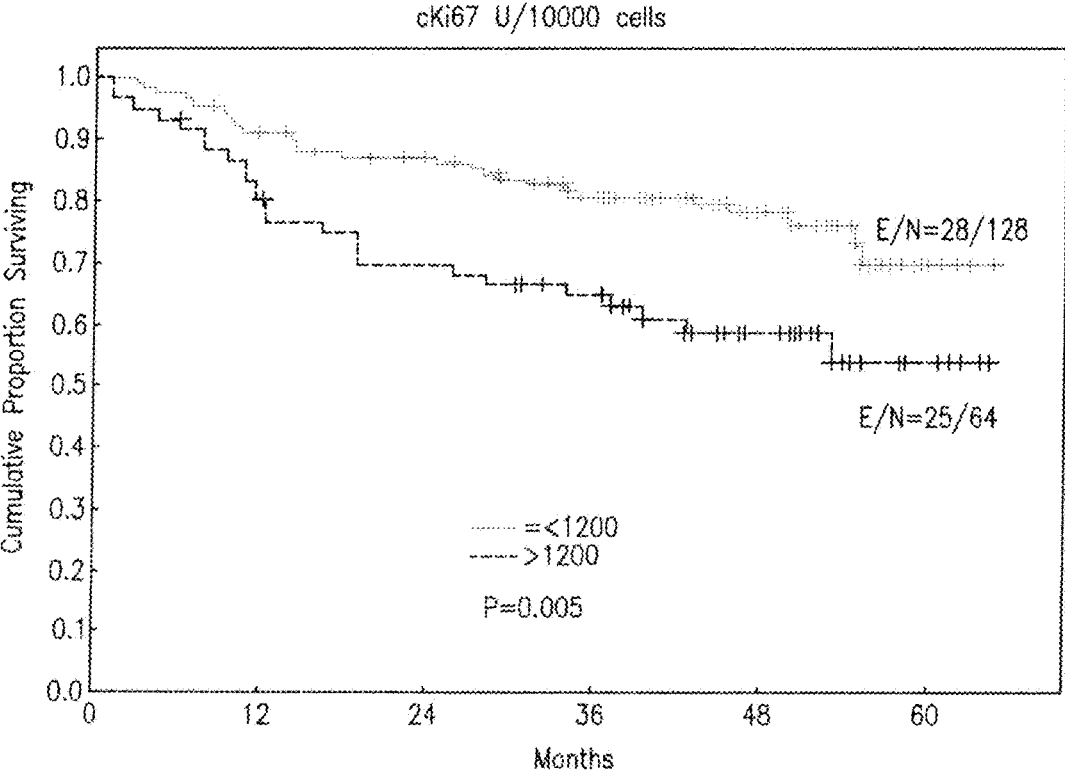

FIG. 15 shows the cumulative proportion of CML patients surviving in two populations of patients: 1) patients having circulating Ki-67 index of less than 1.20 U/1000 lymphocytes (dashed line), and 2) patients having circulating Ki-67 index of Ki-67 protein of greater than 1.20 U/ml (solid line).

DETAILED DESCRIPTION OF THE INVENTION

The present inventions described herein are based on the discovery and characterization that Ki-67 protein can be detected in acellular body fluid samples for the prognosis and diagnosis of certain cancers, including various leukemias.

Exemplary DNA sequence of Ki-67 includes but not limited to GenBank accession number NM_002417. Exemplary amino acid sequence of Ki-67 protein includes GenBank accession number NP_002408 and is provided in FIG. 2 (SEQ ID NO: 1).

The present invention provides methods for detecting the level of Ki-67 protein of an individual. The level of Ki-67 protein is determined by assaying a biological sample from an individual for Ki-67 protein. Ki-67 protein is assayed using assays known in the art and binding agents specific to the markers of interest. The levels of Ki-67 protein in the individual are compared to the levels in normal individuals free from any disorder or compared to another individual having particular disorder. Ki-67 protein levels which deviate from the normal levels can be used to diagnose a disorder or to determine the prognosis or treatment for an existing disorder. Further, changes in the Ki-67 protein levels over time can be used to assess progression of the disorder or success of the treatment thereof.

Plasma or Serum Preparation Methods

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70 degrees centigrade until thawed and used. "Fresh" plasma or serum should be refrigerated or maintained on ice until used, with nucleic acid (e.g., RNA, DNA or total nucleic acid) extraction being performed as soon as possible. Exemplary methods are described below.

Blood can be drawn by standard methods into a collection tube, preferably siliconized glass, either without anticoagulant for preparation of serum, or with EDTA, sodium citrate, heparin, or similar anticoagulants for preparation of plasma. The preferred method if preparing plasma or serum for storage, although not an absolute requirement, is that plasma or serum be first fractionated from whole blood prior to being frozen. This reduces the burden of extraneous intracellular RNA released from lysis of frozen and thawed cells which might reduce the sensitivity of the amplification assay or interfere with the amplification assay through release of inhibitors to PCR such as porphyrins and hematin. "Fresh" plasma or serum may be fractionated from whole blood by centrifugation, using preferably gentle centrifugation at 300-800 times gravity for five to ten minutes, or fractionated by other standard methods. High centrifugation rates capable of fractionating out apoptotic bodies should be avoided.

Determination of Absolute Lymphocyte Count

Absolute counts are calculated by multiplying the total white blood cell count by the percent of the specific cell type of interest. While percentage reports are considered adequate for most patients, absolute values are more important for patients with hematologic disorders.

If lymphocyte or other counts are reported as percentages of the total white blood count (wbc), the absolute values can be calculated as follows: total wbc x % cell type reported/100. This formula can be used for calculating the absolute lymphocyte count, absolute neutrophil count, etc.

An exemplary reference range for total white blood cell counts in healthy individuals is $4.0\text{-}11.0\times10^3$ per microliter. The various types of white blood cells are often expressed as a percentage of the total white blood cell count. Exemplary percentage ranges are as follows:

Basophils—0 to 2%, Eosinophils—0% to 3%, Lymphocytes—25% to 35%, Monocytes—3% to 10%, Neutrophils—50% to 60%.

These percentages are derived from 1) a microscopic examination of blood performed manually in which some hundreds of cells are differentiated from each other (this procedure is called a differential) or 2) a machine scored differentiation based on cell patterns.

By way of example, if the total white count reported is 25,000 and the percentage of lymphocytes reported is 80%, the calculation is as follows: 25,000×80/100. The result is an absolute lymphocyte count of 20,000.

Protein Extraction from Acellular Body Fluids

The Ki-67 protein may be extracted from the acellular body fluid sample by any suitable method including, for example, by immobilization on a solid surface such as microwells, beads or microarray using Ki-67 specific antibodies anchored to the solid surface for detection and quantification.

Plasma purification methods are known in the art such. See e.g., Cohn, E. J., et al, Am. Chem. Soc. 62: 3396-3400. (1940); Cohn, E. J., et al., J. Am. Chem. Soc. 72: 465-474 (1950); Pennell, R. B. Fractionation and isolation of purified components by precipitation methods. p. 9-50. In The Plasma Proteins, Vol. 1. F. W. Putman (ed.). Academic Press, New York (1960); and U.S. Pat. No. 5,817,765.

Antibodies to Ki-67 Protein

Methods of generating antibodies are well known in the art, see, e.g., Sambrook, et al., 1989, Molecular Cloning: A Laboratory Manual, Second Edition, Cold Spring Harbor Press, Plainview, NY. Antibodies for Ki-67 are known in the art and are described, for example, in White, D. M., et al. 47 J. Clin. Pathol. 209-213 (1994); Schwarzenbach, H., et al., 9(5) Breast Cancer Research R66 (2007); Lokhorst, H. M., et al., 69(4) Br. J. Haematology 477-481 (1988); Girino M., et al., 85(1) Acta Haematology 26-30 (1991); and Genbank Accession No. NM 002417.

Antibodies may be detectably labeled by methods known in the art. Labels include, but are not limited to, radioisotopes such as $^3H$, $^{14}C$, $^{35}S$, $^{32}P$, $^{123}I$, $^{125}I$, $^{131}I$), enzymes (e.g., peroxidase, alkaline phosphatase, beta-galactosidase, luciferase, alkaline phosphatase, acetylcholinesterase and glucose oxidase), enzyme substrates, luminescent substances (e.g., luminol), fluorescent substances (e.g., FITC, rhodamine, lanthanide phosphors), biotinyl groups (which can be detected by marked avidin e.g., streptavidin containing a fluorescent marker or enzymatic activity that can be detected by optical or colorimetric methods), predetermined polypeptide epitopes recognized by a secondary reporter (e.g., leucine zipper pair sequences, binding sites for secondary antibodies, metal binding domains, epitope tags) and colored substances. In binding these labeling agents to the antibody, the maleimide method (Kitagawa, T., et al., 79 J. Biochem. 233-236 (1976)), the activated biotin method (Hofmann, K., et al. 100 J. Am. Chem. Soc. 3585 (1978)) or the hydrophobic bond method, for instance, can be used.

In some embodiments, labels are attached via spacer arms of various lengths to reduce potential steric hindrance. Antibodies may also be coupled to electron dense substances, such as ferritin or colloidal gold, which are readily visualized by electron microscopy.

Where a radioactive label is used as a detectable substance, proteins may be localized by autoradiography. The results of autoradiography may be quantitated by determining the density of particles in the autoradiographs by various optical methods, or by counting the grains.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against Ki-67.

Antibodies to Ki-67 protein are available commercially through multiple sources. For example, purified antibodies directed Ki-67 protein are available labeled or unlabeled through Abcam Inc. (Cambridge, MA).

Immunoassays to Detect Ki-67 Protein

Immunoassays, or assays to detect an antigen using an antibody, are well known in the art and can take many forms, e.g., radioimmunoassay, immunoprecipitation, Western blotting, enzyme-linked immunosorbent assay (ELISA), electrochemiluminescence assay, and 2-site or sandwich immunoassay.

In preferred embodiments, a sandwich ELISA is used. In this assay, two antibodies to different segments, or epitopes, of the antigen are used. The first antibody (capture antibody) is coupled to a solid support. When a sample of bodily fluid is contacted with the capture antibody on the solid support, the antigen contained in the bodily fluid is captured on the solid support through a specific interaction between antigen and antibody, resulting in the formation of a complex. Washing of the solid support removes unbound or non-specifically bound antigen. Subsequent exposure of the solid support to a detectably-labeled second antibody (detection antibody) to the antigen (generally to a different epitope than the capture antibody) enables the detection of bound or captured antigen. As would be readily recognized by one of skill in the art, assaying additional markers in parallel to assaying for Ki-67 protein is possible with the use of distinct pairs of specific antibodies, each of which is directed against a different marker. The capture and detection antibodies may be individually monoclonal or polyclonal antibodies.

Relative or actual amounts of Ki-67 protein in body fluids can be determined by methods well known in the art. See e.g., Drach, J., et al., 10(6) Cytometry 743-749 (1989). For example, a standard curve can be obtained in the ELISA using known amounts of Ki-67 protein. The actual amount of the Ki-67 protein in a body fluid may thus be determined using the standard curve. Another approach that does not use a standard curve is to determine the dilution of body fluid that gives a specified amount of signal. The dilution at which 50% of the signal is obtained is often used for this purpose. In this case, the dilution at 50% maximal binding of Ki-67 protein in a patient body fluid is compared with the dilution at 50% of maximal binding for Ki-67 protein obtained in the same assay using a reference sample (i.e., a sample taken from the corresponding bodily fluid of normal individuals, free of proliferative disorders).

Methods of identifying the binding of a specific binding agent to Ki-67 protein are known in the art and vary dependent on the nature of the label. In preferred embodiments, the detectable label is a fluorescent dye. In other embodiments, electrochemiluminescence ("ECL") assay is used for detection of Ki-67 protein. In one embodiment, this ECL assay employs Meso Scale Discovery (MSD®) technology which is an adaptation of ELISA assays. A capture antibody specific for Ki-67 (mouse anti human Ki-67) is coated onto the wells. Nonspecific binding was first blocked by overnight incubation at 4° C. with Blocker A solution provided by the manufacturer. Samples including standards of known Ki-67 concentrations, specimens and controls are diluted, added to the well s and incubated during 2 hours. Plates are washed 3 times to remove the unbound samples and the detection antibody rabbit anti human Ki-67 is added and incubated. After washing to remove the unbound rabbit anti human Ki-67 antibody, SULFO-TAG anti rabbit antibody is added to the wells. The reading is achieved by adding a MSD® Read Buffer solution which contains Tripropylamine (TPA) to the plate. Each sample is measured in duplicate Standard curves for the estimation of Ki-67 concentration are generated by using serial dilutions of HL60 lysate. The plate is read using MSD Sector Imager 2400 Instrument for electrochemiluminescence RLU (relative light unit) signal. This RLU signal is analyzed and compared with RLU signals of standard to get the concentration of each sample.

Diagnosis of Cancer

The level of Ki-67 protein in a test sample can be used in conjunction with clinical factors other than Ki-67 protein to diagnose a disease. In these embodiments, the level of Ki-67 protein measured in the test sample is compared to a reference value to determine if the levels of Ki-67 protein is elevated or reduced relative to a reference value. Preferably, the reference value is the Ki-67 protein level measured in a comparable sample from one or more healthy individuals. An increase or decrease in Ki-67 protein may be used alone or in conjunction with clinical factors other than the level of Ki-67 protein to diagnose a disease.

Clinical factors of particular relevance in the diagnosis of cancer include, but are not limited to, the patient's medical history, a physical examination of the patient, complete blood count, examination of bone marrow cells, cytogenetics, and immunophenotyping of blood cells.

Monitoring Progression and/or Treatment

In one aspect of the invention, the level of Ki-67 protein in biological sample of a patient is used to monitor the effectiveness of treatment. In preferred embodiments, the level of a Ki-67 protein in a test sample obtained from a treated patient, can be compared to the level from a reference sample obtained from that patient prior to initiation of the same treatment. Clinical monitoring of treatment preferably entails that each patient serve as his or her own baseline control.

A decrease in Ki-67 protein in the patient test sample as compared to the patient's reference sample is indicative of an in vivo effect of the treatment at the time the test sample was obtained. In some embodiments, test samples are obtained at multiple time points following administration of the treatment. In these embodiments, measurement of Ki-67 protein in the test samples provides an indication of the extent and duration of in vivo effect of the treatment.

In another aspect of the invention, the level of Ki-67 protein relative to the absolute lymphocytes count in biological sample of a patient is used to monitor the effectiveness of treatment. In preferred embodiments, the level of a Ki-67 protein in a test sample obtained from a treated patient, a ratio of the level of Ki-67 protein to the absolute lymphocyte count is obtained and the ratio can be compared to the ratio from a reference sample obtained from that patient prior to initiation of the same treatment. Clinical monitoring of treatment preferably entails that each patient serve as his or her own baseline control.

A decrease in the ratio of Ki-67 protein to the absolute lymphocytes in the patient test sample as compared to the patient's reference sample is indicative of an in vivo effect of the treatment at the time the test sample was obtained. In some embodiments, test samples are obtained at multiple time points following administration of the treatment. In these embodiments, measurement of the ratio Ki-67 protein to the absolute lymphocytes in the test samples provides an indication of the extent and duration of in vivo effect of the treatment.

Determining Prognosis

Provided herein are methods of using Ki-67 protein level in a test sample from a patient in conjunction with clinical factors in determining the prognosis for a patient having cancer. In some embodiments, prognosis may be a prediction of the likelihood that a patient will survive for a particular period of time, or the prognosis is a prediction of how long a patient may live, or the prognosis is the likelihood that a patent will recover from a disease or disorder. There are many ways that prognosis can be expressed. For example prognosis can be expressed in terms of complete remission rates (CR), overall survival (OS) which is the amount of time from entry to death, remission duration, which is the amount of time from remission to relapse or death.

In certain embodiments high levels of Ki-67 protein are used as indicators of an unfavorable prognosis, for example, in ALL. In another embodiment, high levels of Ki-67 protein are used as indicators of an longer survival time, for example in CML and AML. According to the method, the determination of prognosis can be performed by comparing the measured Ki-67 protein level to levels determined in comparable samples from healthy individuals or to levels known to corresponding with favorable or unfavorable outcomes. The absolute Ki-67 protein levels obtained may depend on a number of factors, including but not limited to the laboratory performing the assays, the assay methods used, the type of body fluid sample used and the type of disease a patient is afflicted with. According to the method, values can be collected from a series of patients with a particular disorder to determine appropriate reference ranges of Ki-67 protein for that disorder. One of ordinary skill in the art is capable of performing a retrospective study that compares the determined Ki-67 protein levels to the observed outcome of the patients and establishing ranges of levels for each activity that can be used to designate the prognosis of the patients with a particular disorder. For example, Ki-67 protein levels in the lowest range would be indicative of a more favorable prognosis, while Ki-67 protein levels in the highest ranges would be indicative of an unfavorable prognosis.

Because the level of Ki-67 protein in a test sample from a patient relates to the prognosis of a patient in a continuous fashion, the determination of prognosis can be performed using statistical analyses to relate the determined activity levels to the prognosis of the patient. A skilled artisan is capable of designing appropriate statistical methods. For example the methods of the present invention may employ the chi-squared test, the Kaplan-Meier method, the log-rank test, multivariate logistic regression analysis, Cox's proportional-hazard model and the like in determining the prognosis. Computers and computer software programs may be used in organizing data and performing statistical analyses.

In some embodiments, a circulating Ki-67 index value is indicative of prognosis such as survival time. A circulating Ki-67 index value may be determined for example, by obtaining a ratio of the Ki-67 protein per 1000 circulating lymphocytes/μl of plasma. In some embodiment, higher circulating Ki-67 index value is indicative of poor prognosis such as in CLL, ALL, AML, CML, AUL.

In certain embodiments, the prognosis of ALL, AML, AUL, CLL or CML patients can be correlated to the clinical outcome of the disease using the level of Ki-67 protein and other clinical factors. Simple algorithms have been described and are readily adapted to this end. The approach by Giles et. al., British Journal of Hemotology, 121:578-585, is exemplary. As in Giles et al., associations between categorical variables (e.g., proteasome activity levels and clinical characteristics) can be assessed via crosstabulation and Fisher's exact test. Unadjusted survival probabilities can be estimated using the method of Kaplan and Meier. The Cox proportional hazards regression model also can be used to assess the ability of patient characteristics (such as proteasome activity levels) to predict survival, with 'goodness of fit' assessed by the Grambsch-Therneau test, Schoenfeld residual plots, martingale residual plots and likelihood ratio statistics (see Grambsch, 1995; Grambsch et al, 1995).

In some embodiments of the invention, multiple prognostic factors, including Ki-67 protein level, are considered when determining the prognosis of a patient. For example, the prognosis of an AML or ALL patient may be determined based on Ki-67 protein and one or more prognostic factors selected from the group consisting of cytogenetics, performance status, AHD (antecedent hematological disease), age, and diagnosis (e.g., MDS v. AML). In certain embodiments, other prognostic factors may be combined with the Ki-67 protein level in the algorithm to determine prognosis with greater accuracy.

Example 1

Figure 4:
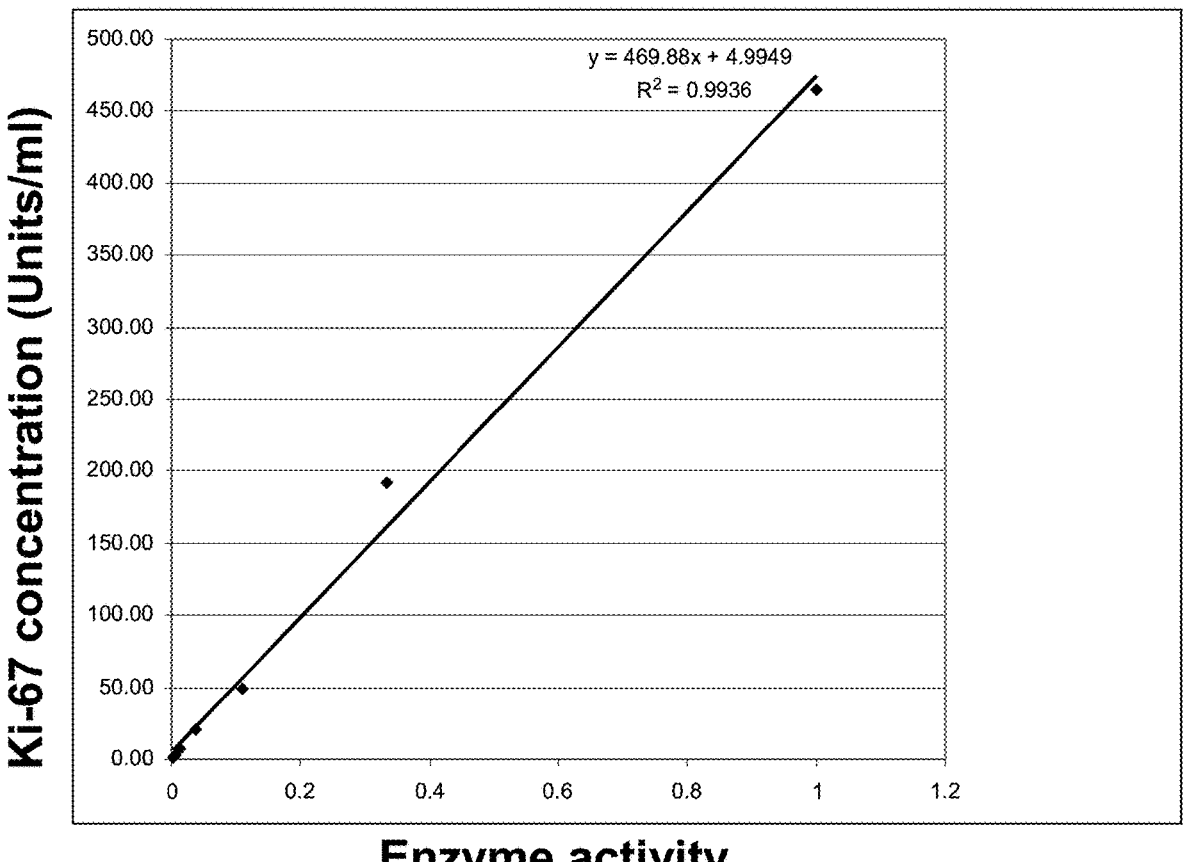
FIG. 4 shows a standard curve for the Ki-67 assay described in Example 1.

Reproducibility of the Assay for Detection of Ki-67 Protein by MSD® Electrochemiluminiscent Method Standard Curve Reproducibility:

Seven standards containing Ki-67 at various concentrations (500, 166.66, 55.55, 18.51, 6.17, 2.15, and 0.68 Units/ml) was run in a daily assay set up to generate a calibration curve. The slope of the curve was used as a conversion factor to calculate enzyme activity. The Ki-67 standard curve showed good linearity ($R^2$) and reproducibility (CV %) (FIG. 4). The standard curve was run on various days over several months and showed excellent reproducibility.

Intra-Assay Variation:

The intra-assay variation is defined as the reproducibility of a sample within an assay. Plasma controls (high and low control) involved 8 replicates to evaluate reproducibility within runs (Table 1). The terms "low," "medium" and "high" refer to relative levels of Ki-67 protein in the plasma samples. The intra-assay CV % for plasma Ki-67 was 5.22% for low normal, 5.56% for low patient and 1.54% for high patient.

TABLE 1

| | | | | | | |
|---|---|---|---|---|---|---|
| | Intra-assay Variation and accuracy | | | | | |
| | Patient | | | Normal | | |
| repeat | low | med | high | low | low | high |
| 1 | 37061 | 171567 | 485095 | 57460 | 5991 | 74363 |
| 2 | 43240 | 174448 | 478073 | 62089 | 6650 | 55567 |
| 3 | 39913 | 167472 | 479059 | 60579 | 6474 | 61129 |
| 4 | 41812 | 161963 | 478472 | 59274 | 6157 | 47193 |
| 5 | 42662 | 161212 | 477979 | 56252 | 5996 | 54721 |
| 6 | 42040 | 158579 | 463003 | 57931 | 5800 | 45820 |
| Mean Ki-67 | 41121.33 | 165873.5 | 476946.8 | 58930.83 | 6178 | 56465.5 |
| STDEV | 2286.034 | 6304.356 | 7347.709 | 2151.623 | 323.0536 | 10442.46 |
| % CV | 5.55924 | 3.800701 | 1.540572 | 3.651098 | 5.229096 | 18.49353 |

In some embodiments, a ratio of the level of Ki-67 protein in acellular body fluid to the absolute lymphocyte count is indicative of prognosis of certain cancers including breast cancer, prostate cancer, lymphoma, and leukemia. The ratio is compared to a cutoff value or a reference value. A ratio of the level of Ki-67 protein in acellular body fluid to the absolute lymphocyte count lower than the cutoff value or a reference value is indicative of better prognosis as compared to a ratio higher than the cutoff or reference value.

Inter-Assay Variation:

The inter-assay variation is defined as the reproducibility of a sample between assays. Five plasma controls (1 high, 2 med, and 2 low Ki-67 levels) were run 6 different days to determine inter-day assay reproducibility (Table 2). The Ki-67 assay has a CV % of less than 15 for the inter assay variation. The CV % for low, medium and high plasma concentration of Ki-67 protein was 4.11% (average of 4.97 and 3.25), 5.75% (average of 6.84 and 4.67) and 9.46%, respectively.

TABLE 2

| | | | | | |
|---|---|---|---|---|---|
| | Inter-Assay Variation and Accuracy | | | | |
| dates | Patient 1 high | Patient 2 med | Patient 3 med | Patient 4 low | Patient 5 low |
| Day 1 | 124986 | 68704 | 46657 | 3826 | 2631 |
| Day 2 | 121214 | 65010 | 42044 | 3493 | 2847 |
| Day 6 | 110414 | 65642 | 41696 | 3759 | 2626 |

TABLE 2-continued

| | | Inter-Assay Variation and Accuracy | | |
|---|---|---|---|---|
| dates | Patient 1 high | Patient 2 med | Patient 3 med | Patient 4 low | Patient 5 low |
|---|---|---|---|---|---|
| Day 8 | 116377 | 68829 | 43876 | 3356 | 2785 |
| Day 10 | 104208 | 63735 | 45903 | 3576 | 2676 |
| Day 14 | 96819 | 56740 | 45398 | 3487 | 2734 |
| Mean Ki-67 | 112336.3 | 64776.67 | 44262.33 | 3582.833 | 2716.5 |
| SD | 10636.79 | 4434.449 | 2067.476 | 178.28 | 88.50932 |
| CV | 9.468702 | 6.84575 | 4.670959 | 4.975951 | 3.258212 |

Selectivity is the ability of an analytical method to differentiate and quantify the analyte in the presence of other components in the sample. For selectivity, analyses of blank samples of the appropriate biological matrix were obtained, tested for interference and selectivity ensured at the lower limit of quantification. The Ki-67 Zero standard was run in 40 replicates each and the selectivity of the assay for detection of Ki-67 by MSD® Electrochemiluminiscent assay was found to be 2996.3 RLU. The limit of detection (LOD) is defined as the concentration of an analyte required to give a signal equal to the background (blank) plus three times the standard deviation of the blank.

Example 2

Serum Starvation Downregulates Ki-67 Protein Expression in Cultured Cells

Figure 6A:
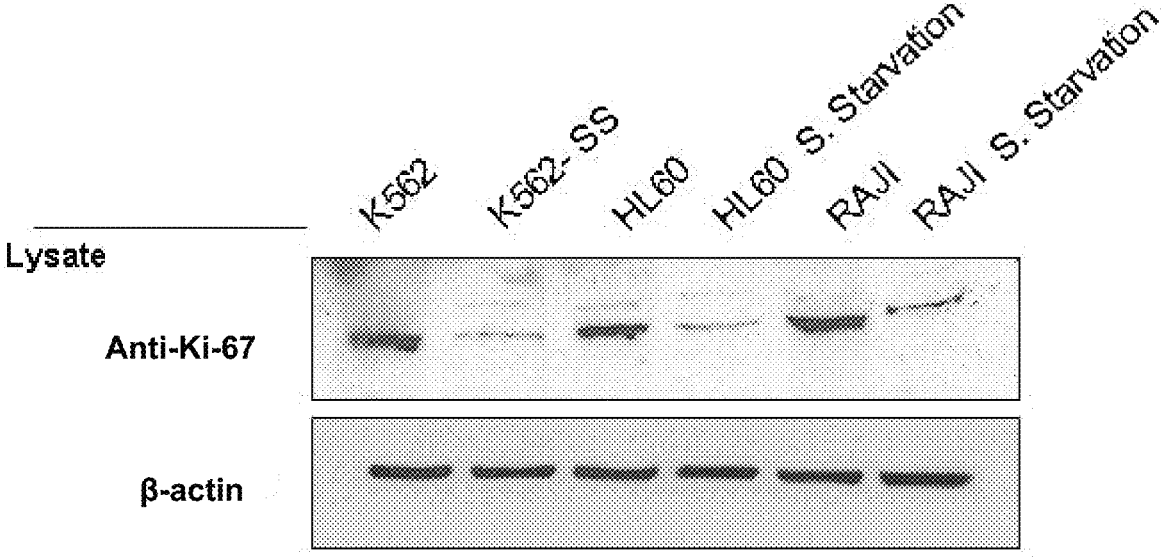
FIGS. 6A and 6B show the effect of serum starvation on the expression level of Ki-67 protein in cultured cells.

K562, HL60, and Raji cells were cultured in media containing 10% FBS or 0.2% FBS. Cell lysates (100 μg) were prepared and analyzed by SDS-PAGE/immunoblotting using anti-Ki-67 or anti-actin antibodies. Antibody detection was accomplished by ECL, with exposure to x-ray film. Ki-67 protein is downregulated under serum starved condition as shown in FIG. 6A.

Figure 6B:
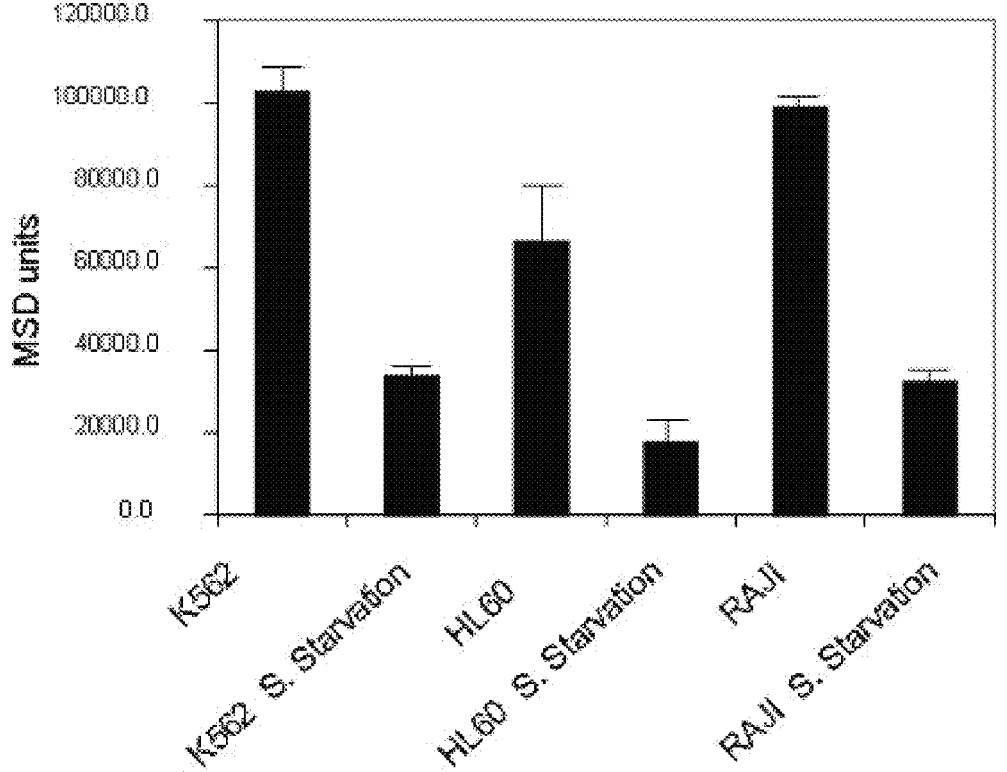

Similar results were obtained when the lysates were also analyzed using MSD® ECL method. Ki-67 protein is downregulated under serum starved condition and shown in FIG. 6B.

Example 3

Detection of Ki-67 Protein in the Plasma of CLL Patients

Figure 5:
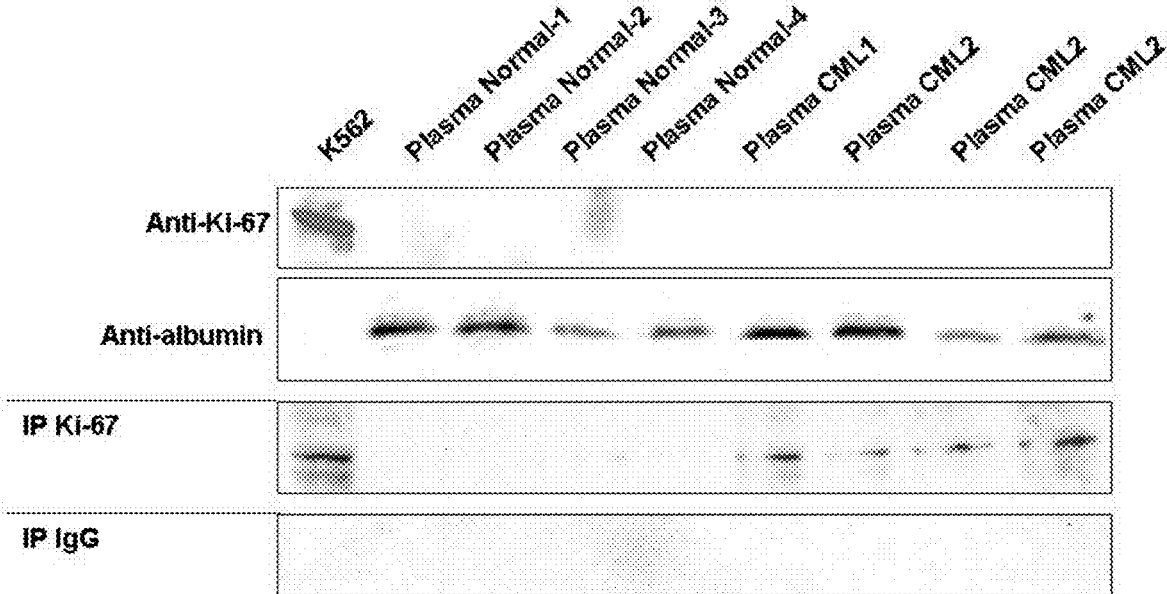
FIG. 5 shows the results of detection of Ki-67 protein in plasma in normal and CML patients by direct Western blotting and by immunoprecipitation followed by Western blotting. Albumin was used as a positive control in direct Western blotting and IgG was used as a negative control for immunoprecipitation by Ki-67 antibody.

Plasma samples were obtained from normal individuals and chronic myelogenous leukemia (CML) patients. The detection of Ki-67 protein in plasma was evaluated by Western blotting (with or without prior immunoprecipitation) with anti-Ki-67 antibody (mouse monoclonal anti-Ki-67 antibody from Invitrogen™, Clone 7B11; and rabbit polyclonal anti-Ki-67 antibody from Santa Cruz Biotechnology, Inc., Clone H300). When Western blotting was performed after immunoprecipitation, the immunoprecipitate was diluted 1:1 in lysis buffer prior to Western blotting. The top row of results in FIG. 5 shows that Ki-67 was not detectable directly in any normal or patient plasma without pre-immunoprecipitation. The second row from the top in FIG. 5 shows that albumin was directly detectable in each plasma sample analyzed.

The bottom two rows in FIG. 5 depict immunoprecipitation of Ki-67 followed by Western blotting using anti-Ki-67 antibody. The results in the third row from the top in FIG. 5 shows that Ki-67 was detectable in CML patient plasma but not in normal plasma.

Following qualitative detection of plasma Ki-67 in CLL patients, the plasma Ki-67 protein was quantified using Meso Scale Discovery (MSD) in the plasma of patients with CLL (n=194) and normal patients (n=96). Ki-67 protein levels were significantly higher in patients with CLL and shown in FIG. 11.

Example 4

Correlation of Circulating Ki-67 Levels with Other Clinical Markers in CLL Patients The absolute plasma Ki-67 levels in CLL patients were correlated to other hematological parameters and CLL markers using the Kruskal-Wallis test and Spearman Rank. As shown in Table 4, there was little or no correlation of plasma Ki-67 protein levels in CLL patients with any of the markers.

TABLE 31

| Patient Characteristics. | |
|---|---|
| Characteristic | % |
|---|---|
| Male | 68 |
| Rai III-IV | 25 |
| Splenomegaly | 28 |
| Hepatomegaly | 4 |
| Lymph nodes | 65 |

| | Median (range) |
|---|---|
| Age | 61 (34-84) |
| WBC ($\times 10^3$/uL) | 21.25 (1.4-321) |
| HGB (g/dL) | 13 (3.3-16.8) |
| B2M (mg/L) | 3.1 (1.4-18.1) |
| Platelets ($\times 10^6$/L) | 177 (4-511) |

TABLE 4

| Correlation of circulating absolute Ki-67 levels with various clinical parameters | | | | |
|---|---|---|---|---|
| Variable | Valid - N | Spearman - R | t(N − 2) | P |
|---|---|---|---|---|
| HGB (g/dL) | 194 | 0.047 | 0.654 | 0.51 |
| PLT ($\times 10^6$/L) | 194 | 0.100 | 1.399 | 0.16 |
| WBC ($\times 10^6$/L) | 194 | 0.021 | 0.287 | 0.77 |
| Lymphocytes (%) | 194 | −0.047 | −0.649 | 0.51 |
| Liver enlargement (cm) | 192 | 0.055 | 0.766 | 0.44 |
| Spleen enlargement (cm) | 187 | 0.023 | 0.314 | 0.75 |
| Lymph node sites - enlarged | 190 | −0.059 | 0.815 | 0.42 |
| B2M (mg/L) | 194 | 0.024 | 0.336 | 0.74 |
| BM Cellularity (%) | 189 | 0.118 | 1.624 | 0.11 |

TABLE 4-continued

Correlation of circulating absolute Ki-67
levels with various clinical parameters

| Variable | Valid - N | Spearman - R | t(N − 2) | P |
|---|---|---|---|---|
| BM-Lymphocytes (%) | 194 | 0.079 | 1.099 | 0.27 |
| RAI Stage | | 0.034 | 0.4667 | 0.64 |
| Albumin | | 0.026 | 0.364 | 0.72 |
| Creatinine (mg/dL) | 193 | −0.091 | −1.265 | 0.21 |
| IgG (mg/dL) | 184 | 0.038 | 0.519 | 0.60 |
| IgA (mg/dL) | 183 | −0.079 | −1.073 | 0.28 |
| IgM (mg/dlL | 184 | 0.010 | 0.134 | 0.89 |
| Total Protein (g/dL) | 58 | −0.202 | −1.541 | 0.13 |
| CD11/CD22 (%) | 194 | −0.036 | −0.501 | 0.62 |
| CD11C (%) | 194 | −0.071 | −0.990 | 0.32 |
| CD22(%) | 194 | 0.019 | 0.262 | 0.79 |

Abbreviations: HGB: hemoglobin; PLT: platelet count; WBC: white blood cell count; B2M: β2 microglobulin; BM: Bone Marrow; Ig, immunoglobulin.

Example 5

Correlation of Circulating Ki-67 Index Values with the Survival of CLL Patients

The hematological parameters and CLL markers measured in Example 5 were normalized to the number of circulating lymphocytes in order to obtain a proliferation fraction. This normalization ensures that the Ki-67 levels reflect leukemic proliferation rather than disease volume. These normalized results are referred to as the Ki-67 index. Specifically, the Ki-67 index value is obtained by measuring the ratio of the level of Ki-67 per 1000 circulating lymphocytes (Ki-67 U/1000 lymphocytes).

TABLE 5

Correlation of circulating Ki-67 index values
with various clinical parameters.

| Variable | Valid - N | Spearman - R | t(N − 2) | P |
|---|---|---|---|---|
| HGB (g/dL) | 194 | 0.022 | 03.310 | 0.756 |
| PLT (×10⁶/L) | 194 | 0.165 | 2.325 | 0.021 |
| WBC (×10⁶/L) | 194 | −0.865 | −23.900 | <0.001 |
| Liver enlargement (cm) | 192 | .071 | 0.981 | 0.328 |
| Spleen enlargement (cm) | 187 | −0.194 | −2.684 | 0.008 |
| Lymph node sites - enlarged | 190 | −0.299 | −4.292 | <0.001 |
| Lymphocytes (%) | 194 | −0.717 | −14.288 | <0.001 |
| B2M (mg/L) | 194 | −0.113 | −1.575 | 0.116 |
| BM Cellularity (%) | 189 | −0.401 | −6.001 | <0.001 |
| BM-Lymphocytes (%) | 194 | −0.525 | −8.567 | <0.001 |
| RAI Stage | 193 | −0.169 | −2.363 | 0.019 |
| Albumin | 193 | −0.067 | −0.929 | 0.354 |
| Creatinine (mg/dL) | 193 | −0.113 | −1.575 | 0.116 |
| IgG (mg/dL) | 184 | 0.009 | 0.125 | 0.900 |
| IgA (mg/dL) | 183 | 0.095 | 1.296 | 0.194 |
| IgM (mg/dlL | 184 | 0.154 | 2.115 | 0.035 |
| Total Protein (g/dL) | 58 | −0.096 | −0.726 | 0.470 |
| CD11/CD22 (%) | 194 | −0.111 | −1.551 | 0.122 |
| CD11C (%) | 194 | −0.152 | −2.140 | 0.033 |
| CD22(%) | 194 | −0.099 | −1.384 | 0.167 |

Abbreviations:
HGB: hemoglobin;
PLT: platelet count;
WBC: white blood cell count;
B2M: β2 microglobulin;
BM: Bone Marrow;
Ig, immunoglobulin.

The circulating Ki-67 index values in CLL patients (n=194) were plotted and shown in FIG. 12 which illustrates the range and population profile of the measured Ki-67 index. As shown in Table 4, there was a significant correlation between the circulating Ki-67 index and several hematological markers including white blood cell count, lymphocyte count, percent of bone marrow lymphocytes, RAI staging, spleen enlargement, and number of lymph node sites. However, the circulating Ki-67 index did not correlate with $IgV_H$ mutation status (p=0.62) in a Wilcoxon paired test. The Ki-67 index, as a continuous variable, was significantly associate with survival in a Cox regression model (p=0.02) and was a predictor of survival when a cut-off value of 1.20 U/1000 lymphocytes was used (p=0.005; log rank test), wherein patients having a higher Ki-67 index values had shorter survival than those with lower Ki-67 index values (FIG. 15).

The association of the Ki-67 index with survival was independent of the $IgV_H$ mutation status (Table 6, Model 1). However, in a multivariate model incorporating the Ki-67 index with β2-microglobulin and $IgV_H$, only the Ki-67 index and β2-microglobulin remained significant predictors of survival (Table 6, Model 2).

TABLE 6

Multivariate Modeling

| | Beta | S.E.M. | t-value | Exponent-beta | Wald-Statist. | p |
|---|---|---|---|---|---|---|
| Model #1 | | | | | | |
| cKi-67 Index | 0.926 | 0.412 | 2.250 | 2.257 | 5.064 | 0.024 |
| $IgV_H$ | −1.152 | 0.541 | −2.129 | 0.316 | 4.533 | 0.033 |
| Model #2 | | | | | | |
| cKi-67 Index | 1.012 | 0.415 | 2.44 | 2.751 | 5.954 | 0.015 |
| $IgV_H$ | −0.800 | 0.551 | −1.453 | 0.449 | 2.111 | 0.146 |
| B2M | 0.287 | 0.062 | 4.599 | 1.332 | 21.151 | <0.001 |

Figure 7:
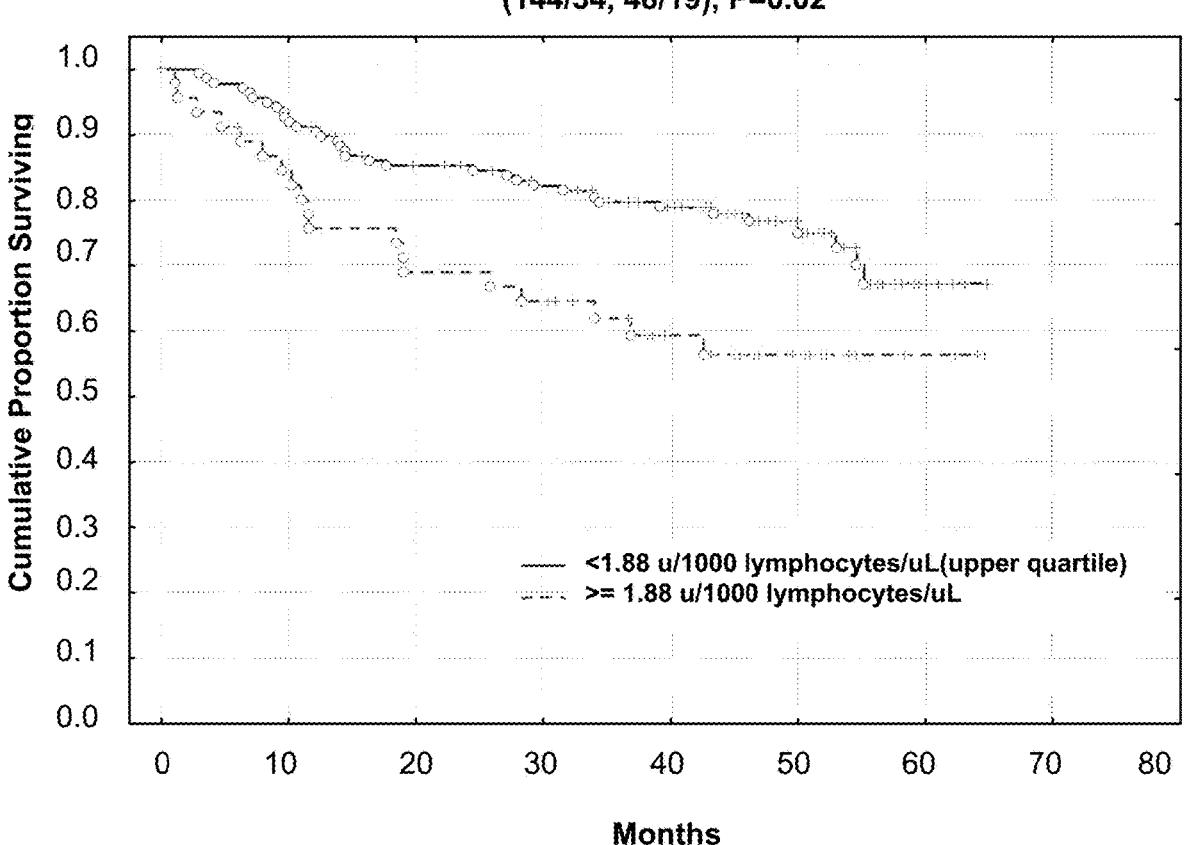
FIG. 7 shows a correlation of survival of CLL patients in months with the normalized level of Ki-67 protein (relative to the number of lymphocytes) in plasma. CLL patients were monitored for survival in months from the time of testing the absolute lymphocyte count and the plasma Ki-67 level of the individual. A normalized Ki-67 value is obtained by taking the ratio of the Ki-67 level to the absolute lymphocyte count. The solid line represents individual with a normalized Ki-67 level of less than 1.88 U/1000 lymphocytes. The broken line represents a normalized Ki-67 value of greater than or equal to 1.88 U/1000 lymphocytes.

In another experiment, CLL patients were divided into two groups: those with a circulating Ki-67 index value of less than 1.88 U/1000 lymphocytes (upper quartile for survival) and those with a circulating Ki-67 index value grater than or equal to 1.88 U/1000 lymphocytes. Cumulative proportion of CLL patients surviving is plotted against months of survival. CLL patients with circulating Ki-67 index value lower than 1.88 U/1000 lymphocytes/µl plasma had higher survival rate than the CLL patients with circulating Ki-67 index value greater than or equal to 1.88 U/1000 lymphocytes/li plasma and shown in FIG. 7

CLL patients were classified based on Rai classification into 5 stages 0, I, II, III, and IV based on increased risk of CLL patients, 0 is the lowest risk and IV has the highest risk. The circulating Ki-67 index value (Ki-67 U/1000 lymphocytes) was plotted against the Rai classifications and indicates a significant prognostic association (FIG. 8). CLL patients with Rai classification of III-IV had the highest relative Ki-67 values while CLL patients with Rai classification of 0 had the lowest relative Ki-67 values. CLL patients with Rai classification of I-II had intermediate Ki-67 values.

Example 6

Association of the Ki-67 Index in CLL Patients Undergoing Chemotherapy

CLL patients were either untreated or treated with Cytoxan, and Fludarabine. Blood samples were collected from CLL patients at the time of initiation of treatment. Some CLL patients in the group had a history of prior treatment, but were off therapy at the time of obtaining blood samples. The circulating Ki-67 index value was obtained and expressed as Ki-67 units per 1000 circulating lympho- cytes. The circulating Ki-67 index value of the treated and untreated CLL groups were plotted. FIG. 9 indicates fol- lowing treatment with Cytoxan, and Fludarabine, CLL patients showed higher levels of circulating Ki-67 index value in plasma as compared to their untreated counterparts.

The Ki-67 index (Ki-67 U/1000 lymphocytes) was mea- sured in CLL patients prior to initiating new therapy. Patients were divided into two groups: those with a normal- ized Ki-67 value of less than 1.88 U/1000 lymphocytes (Group 2) and those with a normalized Ki-67 value grater than or equal to 1.88 units per 1000 lymphocytes (Group 1). Cumulative proportion of CLL patients surviving is plotted against months of survival. As shown in FIG. 10, CLL patients with a circulating Ki-67 index value lower than 1.88 units per 1000 lymphocytes had a higher survival rate than CLL patients with a circulating Ki-67 index value greater than or equal to 1.88 units per 1000 circulating lymphocytes.

Example 7

Ki-67 Protein in Patients with Chronic Myeloid Leukemia

Plasma Ki-67 levels were measured in a study of 81 CML patients in chronic phase and 46 CML patients in acceler- ated/blast phase. Overall, patients with CML had signifi- cantly (P<0.0001) higher levels of Ki-67 in plasma. How- ever, there was no significant difference between accelerated/blast crisis group (median 709.50 U/ml, range: 100-3530.0 U/ml) and the chronic phase group (523 U/ml, range: 73-5857 U/ml) for Ki-67 levels in individual's plasma. Ki-67 levels did not correlate with white cell count or blast count in the chronic phase nor in the accelerated/ blast crisis phase. There was no correlation between Ki-67 levels and response to imatinib therapy. However, patients in the chronic phase with higher levels of Ki-67 (>354 U/ml) had significantly longer survival (P=0.003) as shown in FIG. 14. It possible that higher levels of Ki-67 reflect that more stem cells in these patients are in cell cycle and this may make them more susceptible to chemotherapy. Levels of Ki-67 in patients with accelerated/blast phase did not cor- relate with outcome.

Thus, the data suggests higher proliferation is associated with better survival, most likely confirming that cells in progressing cell cycle may respond better to chemotherapy. This information is important while considering new thera- peutic approaches that target cell cycle.

Example 8

Association of Plasma Ki-67 with Adult Acute Lymphoblastic Leukemia

Figure 1:
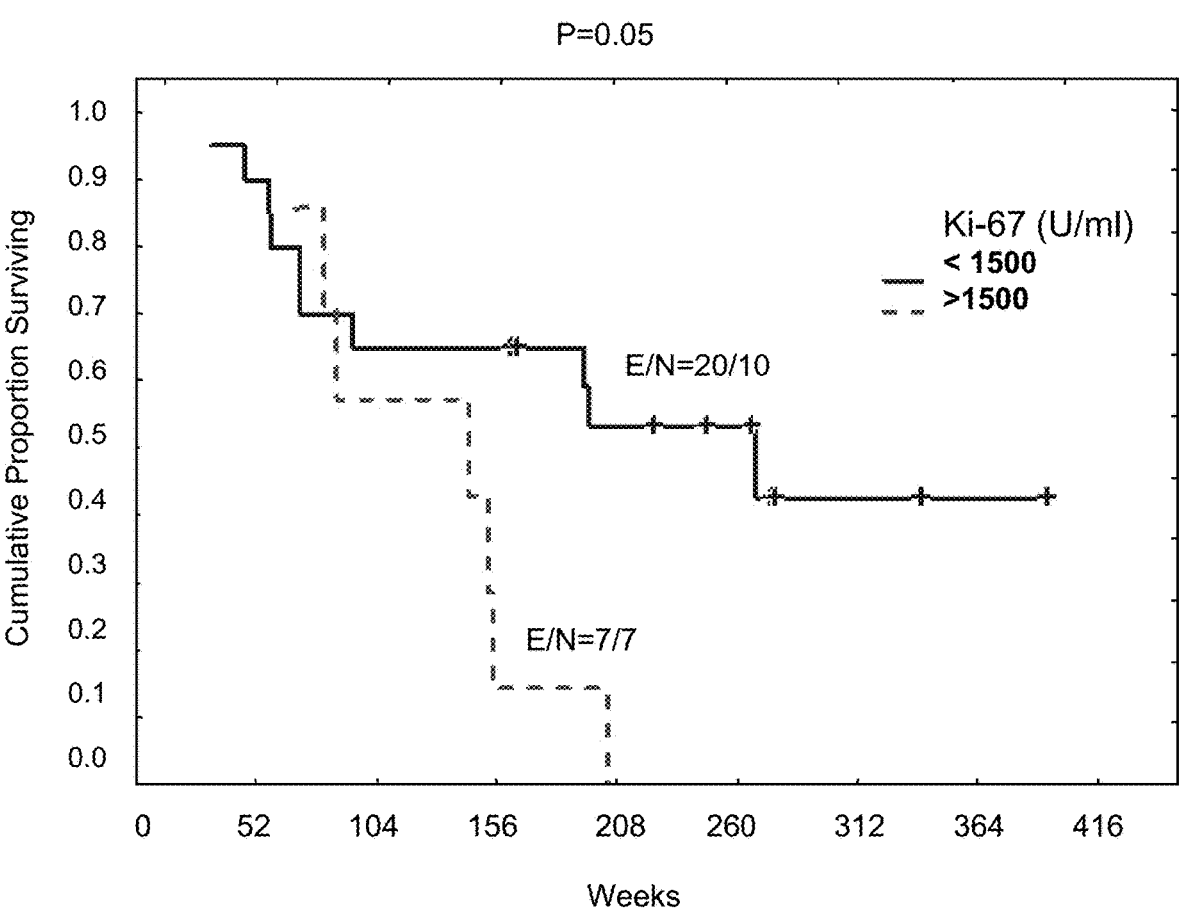
FIG. 1 shows the cumulative proportion of ALL patients surviving in two populations of patients: 1) patients having plasma concentration of Ki-67 protein of less than 1,500 U/ml (solid line), and 2) patients having plasma concentration of Ki-67 protein of greater than 1,500 U/ml (dashed line).
Figure 3:
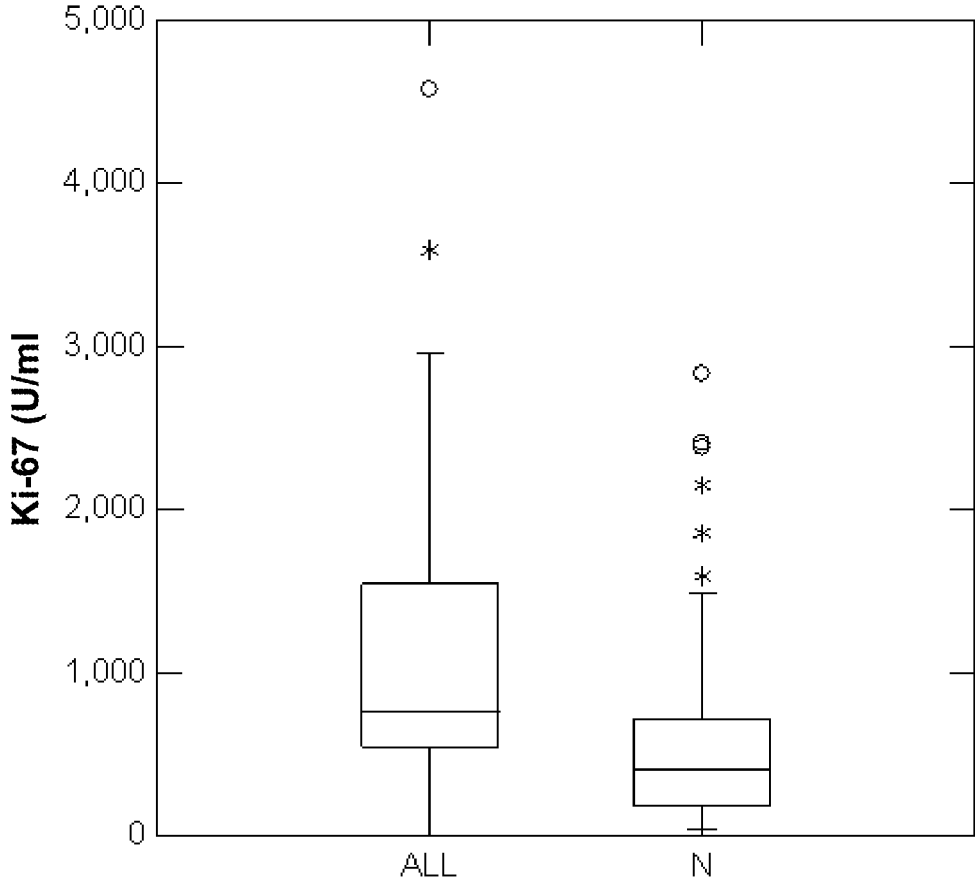
FIG. 3 shows a box plot of the levels of circulating Ki-67 protein in plasma in normal individuals (N) and ALL patients as determined by MSD® Electrochemiluminiscent method. The units of Ki-67 levels are expressed as units/ml (U/ml). Asterisks indicate outliers; open circles indicate extreme values. Median values of the levels of Ki-67 protein is represented as a horizontal line within the box in each case.

Ki-67 protein was measured using Meso Scale Discovery (MSD) and Immunoblot in the plasma of patients with adult acute lymphoblastic leukemia (ALL) (n=27) and normal patients (n=114). Ki-67 protein levels were significantly higher in patients with ALL (median: 762.10 U/ml; range: 0-4574.03 U/ml) than the normal controls (median: 399.2 U/ml; range: 2830.7 U/ml) and shown in FIG. 3. Patients with higher plasma levels of Ki-67 protein had significantly shorter survival than patients with low levels (FIG. 1). Two of the 27 ALL cases were classified as Burkitt's lymphoma and showed high levels of Ki-67 protein in plasma (median: 999 U/ml; range: 1623 U/ml of plasma). Patients older than 70 years of age with ALL had significantly higher Ki-67 protein levels (P=0.05). These data show that measuring Ki-67 protein levels in plasma have a prognostic value in ALL and also demonstrate that Ki-67 protein can be used as a tumor marker in patients with ALL.

In a second study, the Ki-67 level was determined for a group of 106 newly diagnosed AML patients and 98 control. Patients with AML had significantly higher levels of Ki-67 (median: 1300.74 U/ml, range: 0-6789.0 U/ml) as compared with normal control (median: 339.20 U/ml, range: 0-35.76 U/ml) (P<0.00001). The Ki-67 level did not correlate with white cell count, hemoglobin, platelets, LDH, blast count, age, cytogenetic grouping, or performance status. However, patients with high levels of Ki-67 (above the upper quartile of 2100 U/ml) had significantly longer survival in older patient group (>70) (n=84) (P=0.02) as shown in FIG. 13. In addition patients in the poor cytogenetic group (n=38) with >2100 U/ml also had significantly longer survival (P=0.006).

The contents of the articles, patents, and patent applica- tions, and all other documents and electronically available information mentioned or cited herein, are hereby incorpo- rated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suit- ably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be under- stood that although the present invention has been specifi- cally disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric group- ings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method comprising:
   (a) obtaining a plasma sample from a subject suspected of having lymphoma;
   (b) contacting the plasma sample with an agent that binds to a Ki-67 protein that is detectable in the plasma sample, wherein the plasma sample contains less than about 1% (w/w) whole cellular material; and
   (c) detecting a level of Ki-67 protein in the plasma sample by performing an immunoassay, wherein the level of Ki-67 protein is above about 1500 U/mL.

2. The method of claim 1, wherein (a) comprises centrifuging the plasma sample.

3. The method of claim 1, wherein the agent is immobilized on a support.

4. The method of claim 3, wherein the support is a microwell, bead, or microarray.

5. The method of claim 3, wherein the support is nitrocellulose, glass, polyacrylamides, gabbros, or magnetite.

6. The method of claim 3, wherein the support is spherical, cylindrical, or flat.

7. The method of claim 1, wherein the agent is an anti-Ki-67 antibody.

8. The method of claim 7, wherein the anti-Ki-67 antibody is labeled with a detectable label.

9. The method of claim 8, wherein the detectable label is selected from the group consisting of a radioisotope, enzyme, enzyme substrate, luminescent substance, biotinyl group, and predetermined polypeptide epitope recognized by a secondary reporter.

10. The method of claim 1, wherein the Ki-67 protein comprises the amino acid sequence of SEQ ID NO: 1.

11. The method of claim 1, wherein the immunoassay is selected from a radioimmunoassay, immunoprecipitation, Western blot, enzyme-linked immunosorbent assay (ELISA), electrochemiluminescence assay, or 2-site or sandwich immunoassay.

12. The method of claim 1, wherein the lymphoma is non-Hodgkin's lymphoma (NHL) or Burkitt's lymphoma.

13. The method of claim 1, further comprising measuring a level of β2-microglobulin in the plasma sample.

* * * * *

SEQUENCE LISTING

<160> NUMBER OF SEQ ID NOS: 1

<210> SEQ ID NO 1
<211> LENGTH: 3256
<212> TYPE: PRT
<213> ORGANISM: Homo sapiens

<400> SEQUENCE: 1

```
Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
            115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
            180                 185                 190

Arg Asn Ala Ala Asp Pro Ile Ser Gly Asp Phe Lys Glu Ile Ser Ser
            195                 200                 205

Val Lys Leu Val Ser Arg Tyr Gly Glu Leu Lys Ser Val Pro Thr Thr
    210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
            245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
            325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
    355                 360                 365
```

-continued

```
Thr Gly Arg Arg Glu Ser Val Asn Leu Gly Lys Ser Glu Gly Phe Lys
    370             375             380

Ala Gly Asp Lys Thr Leu Thr Pro Arg Lys Leu Ser Thr Arg Asn Arg
385             390             395             400

Thr Pro Ala Lys Val Glu Asp Ala Ala Asp Ser Ala Thr Lys Pro Glu
            405             410             415

Asn Leu Ser Ser Lys Thr Arg Gly Ser Ile Pro Thr Asp Val Glu Val
            420             425             430

Leu Pro Thr Glu Thr Glu Ile His Asn Glu Pro Phe Leu Thr Leu Trp
        435             440             445

Leu Thr Gln Val Glu Arg Lys Ile Gln Lys Asp Ser Leu Ser Lys Pro
        450             455             460

Glu Lys Leu Gly Thr Thr Ala Gly Gln Met Cys Ser Gly Leu Pro Gly
465             470             475             480

Leu Ser Ser Val Asp Ile Asn Asn Phe Gly Asp Ser Ile Asn Glu Ser
            485             490             495

Glu Gly Ile Pro Leu Lys Arg Arg Arg Val Ser Phe Gly Gly His Leu
            500             505             510

Arg Pro Glu Leu Phe Asp Glu Asn Leu Pro Pro Asn Thr Pro Leu Lys
        515             520             525

Arg Gly Glu Ala Pro Thr Lys Arg Lys Ser Leu Val Met His Thr Pro
        530             535             540

Pro Val Leu Lys Lys Ile Ile Lys Glu Gln Pro Gln Pro Ser Gly Lys
545             550             555             560

Gln Glu Ser Gly Ser Glu Ile His Val Glu Val Lys Ala Gln Ser Leu
            565             570             575

Val Ile Ser Pro Pro Ala Pro Ser Pro Arg Lys Thr Pro Val Ala Ser
            580             585             590

Asp Gln Arg Arg Arg Ser Cys Lys Thr Ala Pro Ala Ser Ser Ser Lys
        595             600             605

Ser Gln Thr Glu Val Pro Lys Arg Gly Gly Arg Lys Ser Gly Asn Leu
        610             615             620

Pro Ser Lys Arg Val Ser Ile Ser Arg Ser Gln His Asp Ile Leu Gln
625             630             635             640

Met Ile Cys Ser Lys Arg Arg Ser Gly Ala Ser Glu Ala Asn Leu Ile
            645             650             655

Val Ala Lys Ser Trp Ala Asp Val Val Lys Leu Gly Ala Lys Gln Thr
            660             665             670

Gln Thr Lys Val Ile Lys His Gly Pro Gln Arg Ser Met Asn Lys Arg
        675             680             685

Gln Arg Arg Pro Ala Thr Pro Lys Lys Pro Val Gly Glu Val His Ser
        690             695             700

Gln Phe Ser Thr Gly His Ala Asn Ser Pro Cys Thr Ile Ile Ile Gly
705             710             715             720

Lys Ala His Thr Glu Lys Val His Val Pro Ala Arg Pro Tyr Arg Val
            725             730             735

Leu Asn Asn Phe Ile Ser Asn Gln Lys Met Asp Phe Lys Glu Asp Leu
            740             745             750

Ser Gly Ile Ala Glu Met Phe Lys Thr Pro Val Lys Glu Gln Pro Gln
        755             760             765

Leu Thr Ser Thr Cys His Ile Ala Ile Ser Asn Ser Glu Asn Leu Leu
770             775             780

Gly Lys Gln Phe Gln Gly Thr Asp Ser Gly Glu Glu Pro Leu Leu Pro
```

```
785            790            795            800

Thr Ser Glu Ser Phe Gly Gly Asn Val Phe Phe Ser Ala Gln Asn Ala
            805            810            815

Ala Lys Gln Pro Ser Asp Lys Cys Ser Ala Ser Pro Pro Leu Arg Arg
            820            825            830

Gln Cys Ile Arg Glu Asn Gly Asn Val Ala Lys Thr Pro Arg Asn Thr
            835            840            845

Tyr Lys Met Thr Ser Leu Glu Thr Lys Thr Ser Asp Thr Glu Thr Glu
    850            855            860

Pro Ser Lys Thr Val Ser Thr Ala Asn Arg Ser Gly Arg Ser Thr Glu
865            870            875            880

Phe Arg Asn Ile Gln Lys Leu Pro Val Glu Ser Lys Ser Glu Glu Thr
            885            890            895

Asn Thr Glu Ile Val Glu Cys Ile Leu Lys Arg Gly Gln Lys Ala Thr
            900            905            910

Leu Leu Gln Gln Arg Arg Glu Gly Glu Met Lys Glu Ile Glu Arg Pro
            915            920            925

Phe Glu Thr Tyr Lys Glu Asn Ile Glu Leu Lys Glu Asn Asp Glu Lys
    930            935            940

Met Lys Ala Met Lys Arg Ser Arg Thr Trp Gly Gln Lys Cys Ala Pro
945            950            955            960

Met Ser Asp Leu Thr Asp Leu Lys Ser Leu Pro Asp Thr Glu Leu Met
            965            970            975

Lys Asp Thr Ala Arg Gly Gln Asn Leu Leu Gln Thr Gln Asp His Ala
            980            985            990

Lys Ala Pro Lys Ser Glu Lys Gly Lys Ile Thr Lys Met Pro Cys Gln
        995            1000            1005

Ser Leu Gln Pro Glu Pro Ile Asn Thr Pro Thr His Thr Lys Gln
    1010            1015            1020

Gln Leu Lys Ala Ser Leu Gly Lys Val Gly Val Lys Glu Glu Leu
    1025            1030            1035

Leu Ala Val Gly Lys Phe Thr Arg Thr Ser Gly Glu Thr Thr His
    1040            1045            1050

Thr His Arg Glu Pro Ala Gly Asp Gly Lys Ser Ile Arg Thr Phe
    1055            1060            1065

Lys Glu Ser Pro Lys Gln Ile Leu Asp Pro Ala Ala Arg Val Thr
    1070            1075            1080

Gly Met Lys Lys Trp Pro Arg Thr Pro Lys Glu Glu Ala Gln Ser
    1085            1090            1095

Leu Glu Asp Leu Ala Gly Phe Lys Glu Leu Phe Gln Thr Pro Gly
    1100            1105            1110

Pro Ser Glu Glu Ser Met Thr Asp Glu Lys Thr Thr Lys Ile Ala
    1115            1120            1125

Cys Lys Ser Pro Pro Glu Ser Val Asp Thr Pro Thr Ser Thr
    1130            1135            1140

Lys Gln Trp Pro Lys Arg Ser Leu Arg Lys Ala Asp Val Glu Glu
    1145            1150            1155

Glu Phe Leu Ala Leu Arg Lys Leu Thr Pro Ser Ala Gly Lys Ala
    1160            1165            1170

Met Leu Thr Pro Lys Pro Ala Gly Gly Asp Glu Lys Asp Ile Lys
    1175            1180            1185

Ala Phe Met Gly Thr Pro Val Gln Lys Leu Asp Leu Ala Gly Thr
    1190            1195            1200
```

```
Leu Pro  Gly Ser Lys Arg Gln  Leu Gln Thr Pro Lys  Glu Lys Ala
    1205             1210             1215

Gln Ala  Leu Glu Asp Leu Ala  Gly Phe Lys Glu Leu  Phe Gln Thr
    1220             1225             1230

Pro Gly  His Thr Glu Glu Leu  Val Ala Ala Gly Lys  Thr Thr Lys
    1235             1240             1245

Ile Pro  Cys Asp Ser Pro Gln  Ser Asp Pro Val Asp  Thr Pro Thr
    1250             1255             1260

Ser Thr  Lys Gln Arg Pro Lys  Arg Ser Ile Arg Lys  Ala Asp Val
    1265             1270             1275

Glu Gly  Glu Leu Leu Ala Cys  Arg Asn Leu Met Pro  Ser Ala Gly
    1280             1285             1290

Lys Ala  Met His Thr Pro Lys  Pro Ser Val Gly Glu  Glu Lys Asp
    1295             1300             1305

Ile Ile  Ile Phe Val Gly Thr  Pro Val Gln Lys Leu  Asp Leu Thr
    1310             1315             1320

Glu Asn  Leu Thr Gly Ser Lys  Arg Arg Pro Gln Thr  Pro Lys Glu
    1325             1330             1335

Glu Ala  Gln Ala Leu Glu Asp  Leu Thr Gly Phe Lys  Glu Leu Phe
    1340             1345             1350

Gln Thr  Pro Gly His Thr Glu  Glu Ala Val Ala Ala  Gly Lys Thr
    1355             1360             1365

Thr Lys  Met Pro Cys Glu Ser  Ser Pro Pro Glu Ser  Ala Asp Thr
    1370             1375             1380

Pro Thr  Ser Thr Arg Arg Gln  Pro Lys Thr Pro Leu  Glu Lys Arg
    1385             1390             1395

Asp Val  Gln Lys Glu Leu Ser  Ala Leu Lys Lys Leu  Thr Gln Thr
    1400             1405             1410

Ser Gly  Glu Thr Thr His Thr  Asp Lys Val Pro Gly  Gly Glu Asp
    1415             1420             1425

Lys Ser  Ile Asn Ala Phe Arg  Glu Thr Ala Lys Gln  Lys Leu Asp
    1430             1435             1440

Pro Ala  Ala Ser Val Thr Gly  Ser Lys Arg His Pro  Lys Thr Lys
    1445             1450             1455

Glu Lys  Ala Gln Pro Leu Glu  Asp Leu Ala Gly Leu  Lys Glu Leu
    1460             1465             1470

Phe Gln  Thr Pro Val Cys Thr  Asp Lys Pro Thr Thr  His Glu Lys
    1475             1480             1485

Thr Thr  Lys Ile Ala Cys Arg  Ser Gln Pro Asp Pro  Val Asp Thr
    1490             1495             1500

Pro Thr  Ser Ser Lys Pro Gln  Ser Lys Arg Ser Leu  Arg Lys Val
    1505             1510             1515

Asp Val  Glu Glu Glu Phe Phe  Ala Leu Arg Lys Arg  Thr Pro Ser
    1520             1525             1530

Ala Gly  Lys Ala Met His Thr  Pro Lys Pro Ala Val  Ser Gly Glu
    1535             1540             1545

Lys Asn  Ile Tyr Ala Phe Met  Gly Thr Pro Val Gln  Lys Leu Asp
    1550             1555             1560

Leu Thr  Glu Asn Leu Thr Gly  Ser Lys Arg Arg Leu  Gln Thr Pro
    1565             1570             1575

Lys Glu  Lys Ala Gln Ala Leu  Glu Asp Leu Ala Gly  Phe Lys Glu
    1580             1585             1590
```

-continued

```
Leu Phe Gln Thr Arg Gly His  Thr Glu Glu Ser Met  Thr Asn Asp
    1595              1600              1605

Lys Thr Ala Lys Val Ala Cys  Lys Ser Ser Gln Pro  Asp Pro Asp
    1610              1615              1620

Lys Asn Pro Ala Ser Ser Lys  Arg Arg Leu Lys Thr  Ser Leu Gly
    1625              1630              1635

Lys Val Gly Val Lys Glu Glu  Leu Leu Ala Val Gly  Lys Leu Thr
    1640              1645              1650

Gln Thr Ser Gly Glu Thr Thr  His Thr His Thr Glu  Pro Thr Gly
    1655              1660              1665

Asp Gly Lys Ser Met Lys Ala  Phe Met Glu Ser Pro  Lys Gln Ile
    1670              1675              1680

Leu Asp Ser Ala Ala Ser Leu  Thr Gly Ser Lys Arg  Gln Leu Arg
    1685              1690              1695

Thr Pro Lys Gly Lys Ser Glu  Val Pro Glu Asp Leu  Ala Gly Phe
    1700              1705              1710

Ile Glu Leu Phe Gln Thr Pro  Ser His Thr Lys Glu  Ser Met Thr
    1715              1720              1725

Asn Glu Lys Thr Thr Lys Val  Ser Tyr Arg Ala Ser  Gln Pro Asp
    1730              1735              1740

Leu Val Asp Thr Pro Thr Ser  Ser Lys Pro Gln Pro  Lys Arg Ser
    1745              1750              1755

Leu Arg Lys Ala Asp Thr Glu  Glu Glu Phe Leu Ala  Phe Arg Lys
    1760              1765              1770

Gln Thr Pro Ser Ala Gly Lys  Ala Met His Thr Pro  Lys Pro Ala
    1775              1780              1785

Val Gly Glu Glu Lys Asp Ile  Asn Thr Phe Leu Gly  Thr Pro Val
    1790              1795              1800

Gln Lys Leu Asp Gln Pro Gly  Asn Leu Pro Gly Ser  Asn Arg Arg
    1805              1810              1815

Leu Gln Thr Arg Lys Glu Lys  Ala Gln Ala Leu Glu  Glu Leu Thr
    1820              1825              1830

Gly Phe Arg Glu Leu Phe Gln  Thr Pro Cys Thr Asp  Asn Pro Thr
    1835              1840              1845

Thr Asp Glu Lys Thr Thr Lys  Lys Ile Leu Cys Lys  Ser Pro Gln
    1850              1855              1860

Ser Asp Pro Ala Asp Thr Pro  Thr Asn Thr Lys Gln  Arg Pro Lys
    1865              1870              1875

Arg Ser Leu Lys Lys Ala Asp  Val Glu Glu Glu Phe  Leu Ala Phe
    1880              1885              1890

Arg Lys Leu Thr Pro Ser Ala  Gly Lys Ala Met His  Thr Pro Lys
    1895              1900              1905

Ala Ala Val Gly Glu Glu Lys  Asp Ile Asn Thr Phe  Val Gly Thr
    1910              1915              1920

Pro Val Glu Lys Leu Asp Leu  Leu Gly Asn Leu Pro  Gly Ser Lys
    1925              1930              1935

Arg Arg Pro Gln Thr Pro Lys  Glu Lys Ala Lys Ala  Leu Glu Asp
    1940              1945              1950

Leu Ala Gly Phe Lys Glu Leu  Phe Gln Thr Pro Gly  His Thr Glu
    1955              1960              1965

Glu Ser Met Thr Asp Asp Lys  Ile Thr Glu Val Ser  Cys Lys Ser
    1970              1975              1980

Pro Gln Pro Asp Pro Val Lys  Thr Pro Thr Ser Ser  Lys Gln Arg
```

-continued

```
        1985                1990                1995

Leu Lys  Ile Ser Leu Gly Lys  Val Gly Val Lys Glu  Glu Val Leu
        2000                2005                2010

Pro Val  Gly Lys Leu Thr Gln  Thr Ser Gly Lys Thr  Thr Gln Thr
        2015                2020                2025

His Arg  Glu Thr Ala Gly Asp  Gly Lys Ser Ile Lys  Ala Phe Lys
        2030                2035                2040

Glu Ser  Ala Lys Gln Met Leu  Asp Pro Ala Asn Tyr  Gly Thr Gly
        2045                2050                2055

Met Glu  Arg Trp Pro Arg Thr  Pro Lys Glu Glu Ala  Gln Ser Leu
        2060                2065                2070

Glu Asp  Leu Ala Gly Phe Lys  Glu Leu Phe Gln Thr  Pro Asp His
        2075                2080                2085

Thr Glu  Glu Ser Thr Thr Asp  Asp Lys Thr Thr Lys  Ile Ala Cys
        2090                2095                2100

Lys Ser  Pro Pro Pro Glu Ser  Met Asp Thr Pro Thr  Ser Thr Arg
        2105                2110                2115

Arg Arg  Pro Lys Thr Pro Leu  Gly Lys Arg Asp Ile  Val Glu Glu
        2120                2125                2130

Leu Ser  Ala Leu Lys Gln Leu  Thr Gln Thr Thr His  Thr Asp Lys
        2135                2140                2145

Val Pro  Gly Asp Glu Asp Lys  Gly Ile Asn Val Phe  Arg Glu Thr
        2150                2155                2160

Ala Lys  Gln Lys Leu Asp Pro  Ala Ala Ser Val Thr  Gly Ser Lys
        2165                2170                2175

Arg Gln  Pro Arg Thr Pro Lys  Gly Lys Ala Gln Pro  Leu Glu Asp
        2180                2185                2190

Leu Ala  Gly Leu Lys Glu Leu  Phe Gln Thr Pro Ile  Cys Thr Asp
        2195                2200                2205

Lys Pro  Thr Thr His Glu Lys  Thr Thr Lys Ile Ala  Cys Arg Ser
        2210                2215                2220

Pro Gln  Pro Asp Pro Val Gly  Thr Pro Thr Ile Phe  Lys Pro Gln
        2225                2230                2235

Ser Lys  Arg Ser Leu Arg Lys  Ala Asp Val Glu Glu  Glu Ser Leu
        2240                2245                2250

Ala Leu  Arg Lys Arg Thr Pro  Ser Val Gly Lys Ala  Met Asp Thr
        2255                2260                2265

Pro Lys  Pro Ala Gly Gly Asp  Glu Lys Asp Met Lys  Ala Phe Met
        2270                2275                2280

Gly Thr  Pro Val Gln Lys Leu  Asp Leu Pro Gly Asn  Leu Pro Gly
        2285                2290                2295

Ser Lys  Arg Trp Pro Gln Thr  Pro Lys Glu Lys Ala  Gln Ala Leu
        2300                2305                2310

Glu Asp  Leu Ala Gly Phe Lys  Glu Leu Phe Gln Thr  Pro Gly Thr
        2315                2320                2325

Asp Lys  Pro Thr Thr Asp Glu  Lys Thr Thr Lys Ile  Ala Cys Lys
        2330                2335                2340

Ser Pro  Gln Pro Asp Pro Val  Asp Thr Pro Ala Ser  Thr Lys Gln
        2345                2350                2355

Arg Pro  Lys Arg Asn Leu Arg  Lys Ala Asp Val Glu  Glu Glu Phe
        2360                2365                2370

Leu Ala  Leu Arg Lys Arg Thr  Pro Ser Ala Gly Lys  Ala Met Asp
        2375                2380                2385
```

-continued

```
Thr Pro  Lys Pro Ala Val Ser  Asp Glu Lys Asn Ile  Asn Thr Phe
    2390                 2395              2400

Val Glu  Thr Pro Val Gln Lys  Leu Asp Leu Leu Gly  Asn Leu Pro
    2405                 2410              2415

Gly Ser  Lys Arg Gln Pro Gln  Thr Pro Lys Glu Lys  Ala Glu Ala
    2420                 2425              2430

Leu Glu  Asp Leu Val Gly Phe  Lys Glu Leu Phe Gln  Thr Pro Gly
    2435                 2440              2445

His Thr  Glu Glu Ser Met Thr  Asp Asp Lys Ile Thr  Glu Val Ser
    2450                 2455              2460

Cys Lys  Ser Pro Gln Pro Glu  Ser Phe Lys Thr Ser  Arg Ser Ser
    2465                 2470              2475

Lys Gln  Arg Leu Lys Ile Pro  Leu Val Lys Val Asp  Met Lys Glu
    2480                 2485              2490

Glu Pro  Leu Ala Val Ser Lys  Leu Thr Arg Thr Ser  Gly Glu Thr
    2495                 2500              2505

Thr Gln  Thr His Thr Glu Pro  Thr Gly Asp Ser Lys  Ser Ile Lys
    2510                 2515              2520

Ala Phe  Lys Glu Ser Pro Lys  Gln Ile Leu Asp Pro  Ala Ala Ser
    2525                 2530              2535

Val Thr  Gly Ser Arg Arg Gln  Leu Arg Thr Arg Lys  Glu Lys Ala
    2540                 2545              2550

Arg Ala  Leu Glu Asp Leu Val  Asp Phe Lys Glu Leu  Phe Ser Ala
    2555                 2560              2565

Pro Gly  His Thr Glu Glu Ser  Met Thr Ile Asp Lys  Asn Thr Lys
    2570                 2575              2580

Ile Pro  Cys Lys Ser Pro Pro  Pro Glu Leu Thr Asp  Thr Ala Thr
    2585                 2590              2595

Ser Thr  Lys Arg Cys Pro Lys  Thr Arg Pro Arg Lys  Glu Val Lys
    2600                 2605              2610

Glu Glu  Leu Ser Ala Val Glu  Arg Leu Thr Gln Thr  Ser Gly Gln
    2615                 2620              2625

Ser Thr  His Thr His Lys Glu  Pro Ala Ser Gly Asp  Glu Gly Ile
    2630                 2635              2640

Lys Val  Leu Lys Gln Arg Ala  Lys Lys Lys Pro Asn  Pro Val Glu
    2645                 2650              2655

Glu Glu  Pro Ser Arg Arg Arg  Pro Arg Ala Pro Lys  Glu Lys Ala
    2660                 2665              2670

Gln Pro  Leu Glu Asp Leu Ala  Gly Phe Thr Glu Leu  Ser Glu Thr
    2675                 2680              2685

Ser Gly  His Thr Gln Glu Ser  Leu Thr Ala Gly Lys  Ala Thr Lys
    2690                 2695              2700

Ile Pro  Cys Glu Ser Pro Pro  Leu Glu Val Val Asp  Thr Thr Ala
    2705                 2710              2715

Ser Thr  Lys Arg His Leu Arg  Thr Arg Val Gln Lys  Val Gln Val
    2720                 2725              2730

Lys Glu  Glu Pro Ser Ala Val  Lys Phe Thr Gln Thr  Ser Gly Glu
    2735                 2740              2745

Thr Thr  Asp Ala Asp Lys Glu  Pro Ala Gly Glu Asp  Lys Gly Ile
    2750                 2755              2760

Lys Ala  Leu Lys Glu Ser Ala  Lys Gln Thr Pro Ala  Pro Ala Ala
    2765                 2770              2775
```

-continued

```
Ser Val  Thr Gly Ser Arg Arg  Arg Pro Arg Ala Pro  Arg Glu Ser
    2780                 2785                 2790

Ala Gln  Ala Ile Glu Asp Leu  Ala Gly Phe Lys Asp  Pro Ala Ala
    2795                 2800                 2805

Gly His  Thr Glu Glu Ser Met  Thr Asp Asp Lys Thr  Thr Lys Ile
    2810                 2815                 2820

Pro Cys  Lys Ser Ser Pro Glu  Leu Glu Asp Thr Ala  Thr Ser Ser
    2825                 2830                 2835

Lys Arg  Arg Pro Arg Thr Arg  Ala Gln Lys Val Glu  Val Lys Glu
    2840                 2845                 2850

Glu Leu  Leu Ala Val Gly Lys  Leu Thr Gln Thr Ser  Gly Glu Thr
    2855                 2860                 2865

Thr His  Thr Asp Lys Glu Pro  Val Gly Glu Gly Lys  Gly Thr Lys
    2870                 2875                 2880

Ala Phe  Lys Gln Pro Ala Lys  Arg Lys Leu Asp Ala  Glu Asp Val
    2885                 2890                 2895

Ile Gly  Ser Arg Arg Gln Pro  Arg Ala Pro Lys Glu  Lys Ala Gln
    2900                 2905                 2910

Pro Leu  Glu Asp Leu Ala Ser  Phe Gln Glu Leu Ser  Gln Thr Pro
    2915                 2920                 2925

Gly His  Thr Glu Glu Leu Ala  Asn Gly Ala Ala Asp  Ser Phe Thr
    2930                 2935                 2940

Ser Ala  Pro Lys Gln Thr Pro  Asp Ser Gly Lys Pro  Leu Lys Ile
    2945                 2950                 2955

Ser Arg  Arg Val Leu Arg Ala  Pro Lys Val Glu Pro  Val Gly Asp
    2960                 2965                 2970

Val Val  Ser Thr Arg Asp Pro  Val Lys Ser Gln Ser  Lys Ser Asn
    2975                 2980                 2985

Thr Ser  Leu Pro Pro Leu Pro  Phe Lys Arg Gly Gly  Gly Lys Asp
    2990                 2995                 3000

Gly Ser  Val Thr Gly Thr Lys  Arg Leu Arg Cys Met  Pro Ala Pro
    3005                 3010                 3015

Glu Glu  Ile Val Glu Glu Leu  Pro Ala Ser Lys Lys  Gln Arg Val
    3020                 3025                 3030

Ala Pro  Arg Ala Arg Gly Lys  Ser Ser Glu Pro Val  Val Ile Met
    3035                 3040                 3045

Lys Arg  Ser Leu Arg Thr Ser  Ala Lys Arg Ile Glu  Pro Ala Glu
    3050                 3055                 3060

Glu Leu  Asn Ser Asn Asp Met  Lys Thr Asn Lys Glu  Glu His Lys
    3065                 3070                 3075

Leu Gln  Asp Ser Val Pro Glu  Asn Lys Gly Ile Ser  Leu Arg Ser
    3080                 3085                 3090

Arg Arg  Gln Asn Lys Thr Glu  Ala Glu Gln Gln Ile  Thr Glu Val
    3095                 3100                 3105

Phe Val  Leu Ala Glu Arg Ile  Glu Ile Asn Arg Asn  Glu Lys Lys
    3110                 3115                 3120

Pro Met  Lys Thr Ser Pro Glu  Met Asp Ile Gln Asn  Pro Asp Asp
    3125                 3130                 3135

Gly Ala  Arg Lys Pro Ile Pro  Arg Asp Lys Val Thr  Glu Asn Lys
    3140                 3145                 3150

Arg Cys  Leu Arg Ser Ala Arg  Gln Asn Glu Ser Ser  Gln Pro Lys
    3155                 3160                 3165

Val Ala  Glu Glu Ser Gly Gly  Gln Lys Ser Ala Lys  Val Leu Met
```

-continued

```
      3170              3175              3180

Gln Asn  Gln Lys Gly Lys Gly  Glu Ala Gly Asn Ser  Asp Ser Met
      3185              3190              3195

Cys Leu  Arg Ser Arg Lys Thr  Lys Ser Gln Pro Ala  Ala Ser Thr
      3200              3205              3210

Leu Glu  Ser Lys Ser Val Gln  Arg Val Thr Arg Ser  Val Lys Arg
      3215              3220              3225

Cys Ala  Glu Asn Pro Lys Lys  Ala Glu Asp Asn Val  Cys Val Lys
      3230              3235              3240

Lys Ile  Arg Thr Arg Ser His  Arg Asp Ser Glu Asp  Ile
      3245              3250              3255
```